US006221102B1

(12) United States Patent
Baker et al.

(10) Patent No.: US 6,221,102 B1
(45) Date of Patent: *Apr. 24, 2001

(54) INTRALUMINAL GRAFTING SYSTEM

(75) Inventors: Steven G. Baker, Sunnyvale; Dinah B. Quiachon, San Jose; Alec A. Piplani, Mountain View; Wesley D. Sterman, San Francisco; Ronald G. Williams, Menlo Park, all of CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/485,481

(22) Filed: Jun. 7, 1995

Related U.S. Application Data

(63) Continuation-in-part of application No. 08/420,623, filed on Apr. 12, 1995, now Pat. No. 5,562,728, which is a continuation of application No. 08/109,162, filed on Aug. 19, 1993, now abandoned, which is a division of application No. 07/553,530, filed on Jul. 19, 1990, now Pat. No. 5,275,622, which is a continuation-in-part of application No. 07/166,093, filed on Mar. 19, 1988, now Pat. No. 5,104,399, which is a continuation-in-part of application No. 06/940,907, filed on Dec. 10, 1986, now Pat. No. 4,787,899, which is a continuation of application No. 06/559,935, filed on Dec. 9, 1983, now abandoned.

(51) Int. Cl.$^7$ .................................................. A61F 2/06
(52) U.S. Cl. ......................................... 623/1.36; 623/1.13
(58) Field of Search .................................. 623/1, 11, 12, 623/1.13, 1.36; 606/191, 194, 198, 108

(56) References Cited

U.S. PATENT DOCUMENTS

| 3,562,820 | 2/1971 | Braun . | |
|---|---|---|---|
| 3,657,744 | * 4/1972 | Ersek | ................................ 3/1 |
| 4,130,904 | 12/1978 | Whalen . | |
| 4,140,126 | 2/1979 | Choudhury . | |
| 4,214,587 | * 7/1980 | Sakura, Jr. | ........................... 128/334 |
| 4,580,568 | 4/1986 | Gianturco . | |
| 4,798,606 | 1/1989 | Pinchuk | ................................... 623/1 |
| 4,892,539 | * 1/1990 | Koch | ...................................... 623/1 |
| 5,104,404 | 4/1992 | Wolff | ..................................... 623/1 |
| 5,178,630 | * 1/1993 | Schmitt | ................................. 623/1 |
| 5,562,728 | * 10/1996 | Lazarus et al. | ........................ 623/1 |

FOREIGN PATENT DOCUMENTS

| 0 423 916 A1 | 4/1991 | (EP) . |
| 0 539 237 A1 | 4/1993 | (EP) . |
| 1217402 | 5/1984 | (SU) . |
| 13188235 A1 | 6/1987 | (SU) . |
| 1389778 A2 | 4/1988 | (SU) . |
| 1457921 A1 | 2/1989 | (SU) . |
| 1482714 A2 | 5/1989 | (SU) . |

* cited by examiner

Primary Examiner—Michael J. Milano
Assistant Examiner—Hieu Phan
(74) Attorney, Agent, or Firm—Fulwider Patton Lee & Utecht, LLP

(57) ABSTRACT

An intraluminal grafting system having a delivery catheter comprising a flexible elongate tubular member having proximal and distal extremities and a capsule mounted on the distal extremity of the tubular member and including a graft disposed within the capsule. The graft is comprised of a tubular body configured to be secured to a blood vessel by a self expanding attachment system. The attachment system comprises a generally sinusoidal wire frame having apices which extend longitudinally outward from the end of the tubular body apices which are secured within the tubular body. Both the protruding apices and the base apices are formed with helices which bias the attachment system radially outward. The attachment system further includes a plurality of lumen piercing members that are oriented in a responsive relationship to the radially outward bias of the attachment system. Furthermore, the graft may be configured with a plurality of synthetic fiber tufts secured to the outer surface of the tubular body to facilitate sealing the graft within the vessel. The graft may also include a plurality of crimps formed in the tubular body of the graft.

105 Claims, 15 Drawing Sheets

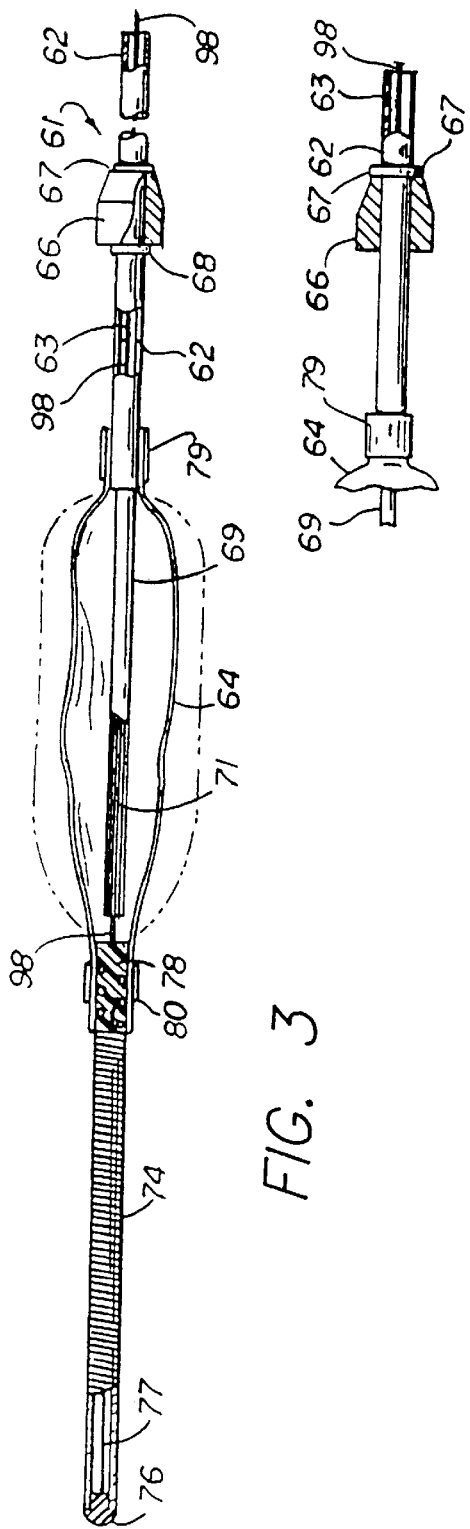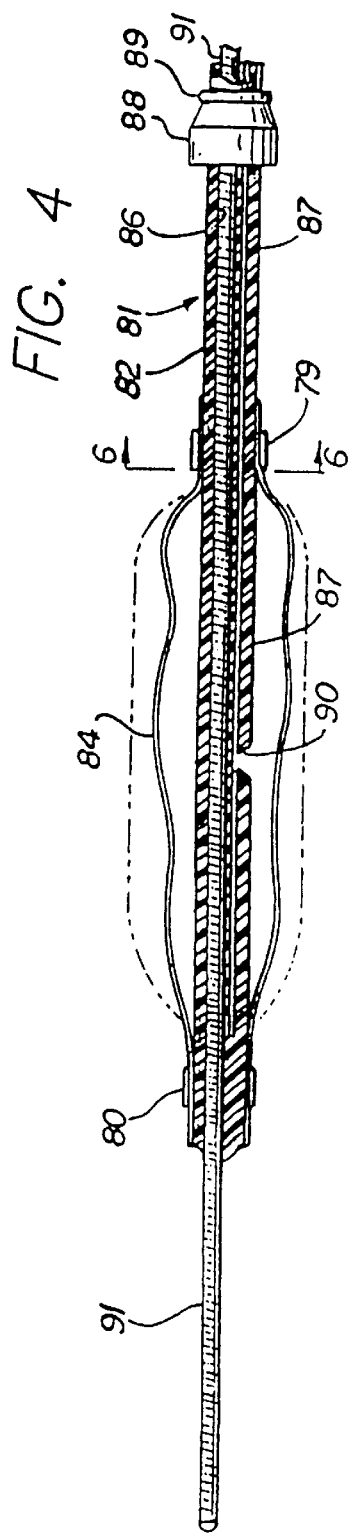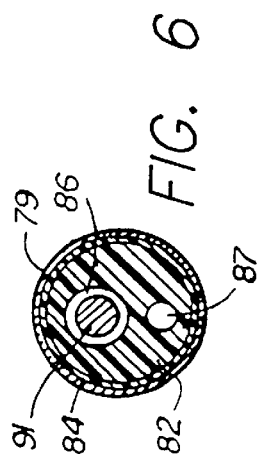

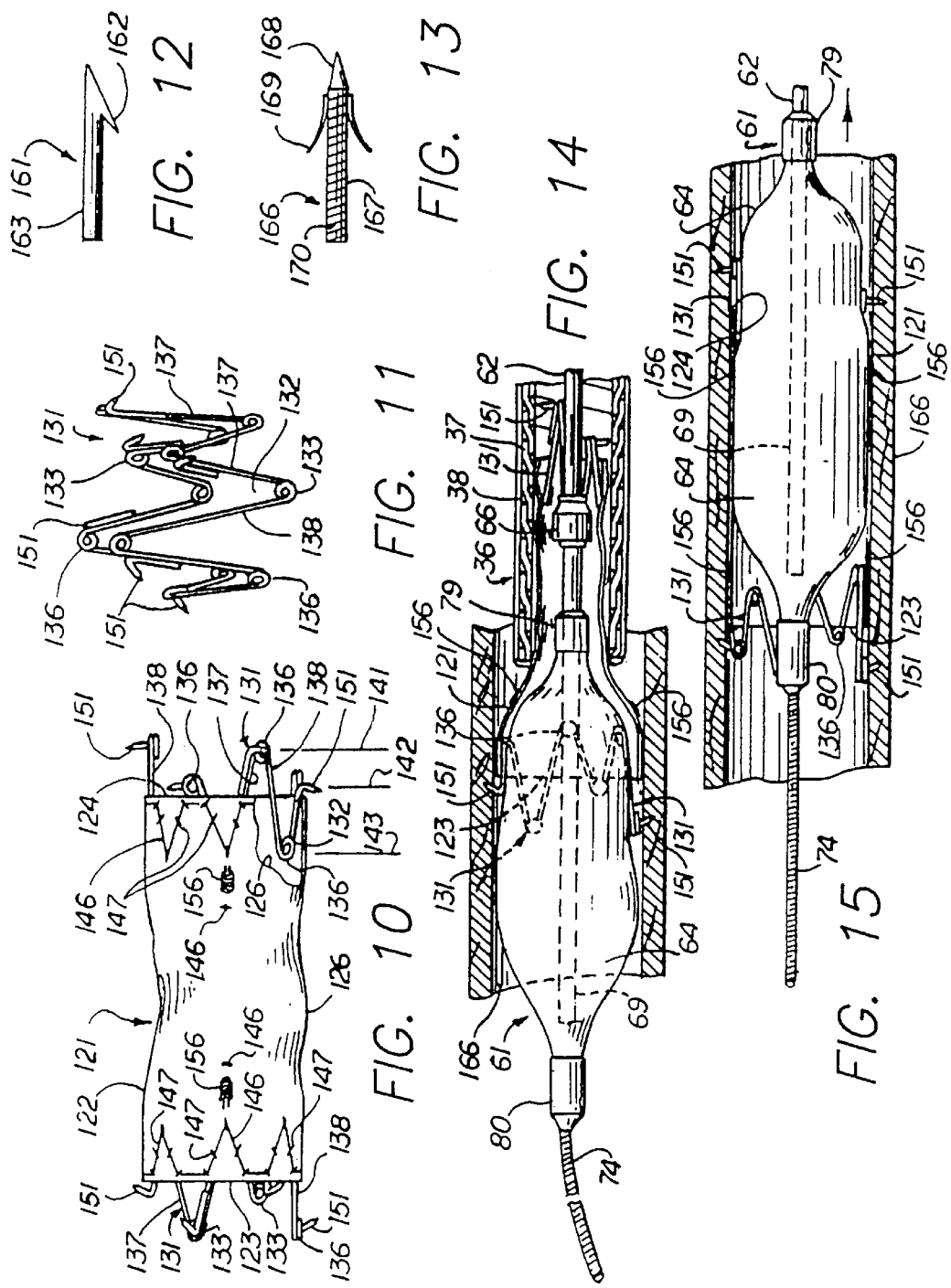

INTRALUMINAL GRAFTING SYSTEM

This application is a continuation-in-part of application Ser. No. 420,623 filed Apr. 12, 1995, now U.S. Pat. No. 5,562,728, which is a continuation of application Ser. No. 109,162 filed Aug. 19, 1993, now abandoned which is a divisional of application Ser. No. 553,530 filed Jul. 13, 1990, now U.S. Pat. No. 5,275,622, which is a continuation-in-part of application Ser. No. 166,093 filed on Mar. 9, 1988, now U.S. Pat. No. 5,104,399, which is a continuation-in-part of application Ser. No. 940,907 filed on Dec. 10, 1986, now U.S. Pat. No. 4,787,899, which is a continuation of application Ser. No. 559,935 filed on Dec. 9, 1983, now abandoned. The contents of each of these applications are hereby incorporated by reference.

BACKGROUND OF THE INVENTION

This application relates to endovascular grafting apparatus, system and method and devices for use therewith.

The state of the art is described in the background of the invention in U.S. Pat. No. 4,787,899.

SUMMARY OF THE INVENTION

In general, it is an object of the present invention to provide an endovascular grafting apparatus, system and method and devices for use therewith which overcome the disadvantages of the prior art apparatus, systems and devices.

Another object of the invention is to provide an apparatus and system of the above character which utilizes a pusher rod assembly which is constrained so that relatively great forces can be applied by the pusher rod assembly.

Another object of the invention is to provide an apparatus and system of the above character in which the capsule is flexible so that it can negotiate bends in the vessels of a patient.

Another object of the invention is to provide a grafting apparatus and system which utilizes a flexible capsule which can contain a graft with hook-like elements without any danger of the hook-like elements penetrating the capsule.

Another object of the invention is to provide an apparatus and system of the above character in which the graft automatically springs into an open or expanded position when it is released from the capsule.

Another object of the invention is to provide an apparatus, system and method of the above character in which a pushing force is applied to the distal extremity of the balloon for advancing a graft out of the capsule.

Another object of the invention is to provide an apparatus and system of the above character in which a fixed wire or an over-the-wire guide wire system can be used.

Another object of the invention is to provide an apparatus and system of the above character in which the graft can be compressed to a very small size in a flexible capsule.

Additional objects and features of the invention will appear in the following description in conjunction with the accompanying drawings.

Another feature of the present invention is a novel attachment system that comprises a sinusoidal wire frame and V-shaped lumen piercing members. The sinusoidal frame has two ends and alternating base apices and protruding apices. The protruding apices protrude outward and are mounted onto the graft to extend outward past the end of the graft. The base apices are oriented inside the lumen of the graft and points inward from the end of the graft. The portion of the wire frame connecting the protruding apices to the base apices are struts.

In one embodiment, the two ends of the wire frame are welded together to obtain circular continuity of the wire frame. In another embodiment, the wire frame has one additional protruding apex and the ends of the wire frame terminate in helices generally aligned with the base helices. The frame is mounted by overlapping the two ends of the wire including a pair of protruding apices adjacent the end. The wire frame is sewn to the body of the graft at various points over the entire wire frame. The lengths of the struts may be adjusted to stagger the apices so that the profile of the wire frame and the graft can be minimized to fit into a smaller delivery capsule.

In addition to the wire frame, the attachment system further includes a plurality of lumen piercing members affixed to the struts. The lumen piercing members are configured to protrude radially outward from the attachment system to engage the lumen wall of a blood vessel and secure the graft in place to prevent migration of the graft along the blood vessel. The lumen piercing member of one embodiment includes a wire arm that has an outwardly protruding hook constructed of stainless steel wire. The hooks are aligned with and welded to the struts of the wire frame.

Another embodiment of the lumen piercing members eliminates the need for welds to secure the lumen piercing members to the graft. Each lumen piercing member is bent into a V-shape and each have an apex and two arms that extend in a direction parallel to the struts of the wire frame. The arms terminate in radially outward protruding hooks that are configured to engage the wall of the vessel. The lumen piercing member is secured to the graft in close proximity to the wire frame and is responsive to the outward bias of the wire frame.

Another embodiment of the attachment system of the present invention configured for use in the iliac arteries in a bifurcated graft includes two sinusoidal wire frames that have alternating base apices and protruding apices. Each of the iliac wire frames have two end arms that extend longitudinally outward to engage the iliac artery wall. The wire arms are configured as lumen piercing members which extend as struts from the end base apices. The two wire frames are joined together by overlying the end base apex of one of the wire frames with the end base apex from the other wire frame such that each of the wire arms extend parallel to an adjacent strut. The end arms are twisted around the adjacent struts and bent behind the protruding strut that is integrally connected to the adjacent strut. The ends of the lumen piercing member is hook-like to securely engage the vessel wall. The hooks are secured to the vessel wall when an additional radially outward force presses the vessel into the lumen wall, such as from a deployment balloon.

Another feature of the present invention includes a device to substantially eliminate leaks around the perimeter of the graft at the ends where the attachment system engages the lumen wall. The outside of the graft is textured with a plurality of filaments or fibers that are spun, woven, knotted, pressed or otherwise loosely associated to form a puffed textured filler or tuft that is sewn to or affixed to the outside of the graft proximal to the end of the graft. The ends of the fibers may be frayed to increase the surface area of the tuft. Alternatively, strands of loosely spun synthetic yarn are cross-stitched around the perimeter of the graft proximate the attachment system.

Another feature of the present invention includes a graft that is crimped radially along at least a portion of the length of the graft. The crimps form a generally corrugated tubular surface defining a plurality of radially outwardly protruding ribs that are separated longitudinally by alternating inwardly directed folds or pleats. The crimping occurs along the length of the graft between the two attachment systems. The crimping may be configured over the entire length or over only a portion of the graft.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 3 is a side elevational view partially in cross section showing a balloon catheter assembly incorporating the present invention.

FIG. 4 is a partial side elevational view in cross section of a portion of an alternative balloon catheter assembly incorporating the present invention showing the use of a movable pusher button capsule of sliding over a limited range.

FIG. 5 is a side elevational view partially in cross section of another alternative embodiment of a balloon catheter assembly incorporating the present invention showing the use of a movable guide wire.

FIG. 6 is a cross sectional view taken along the line 6—6 of FIG. 5.

FIG. 10 is a side elevational view of a graft incorporating the present invention.

FIG. 11 is an enlarged isometric view showing one of the spring attachment means utilized on the graft.

FIG. 12 is a partial enlarged view of an alternative hook-like element utilized in the spring attachment means of FIG. 11.

FIG. 13 is an enlarged view showing another embodiment of a hook-like element used in the spring attachment means of FIG. 11.

FIG. 14 is a side elevational view partially in cross section showing the manner in which the graft is held in the capsule after ejection of the proximal extremity of the graft from the capsule.

FIG. 15 is a view similar to FIG. 14 but showing the proximal and distal extremities of the graft outside of the capsule with the balloon retracted so that it is within the graft and inflated to force the distal attachment means into the vessel wall.

DETAILED DESCRIPTION OF THE PREFERRED EMBODIMENTS

Figure 1:
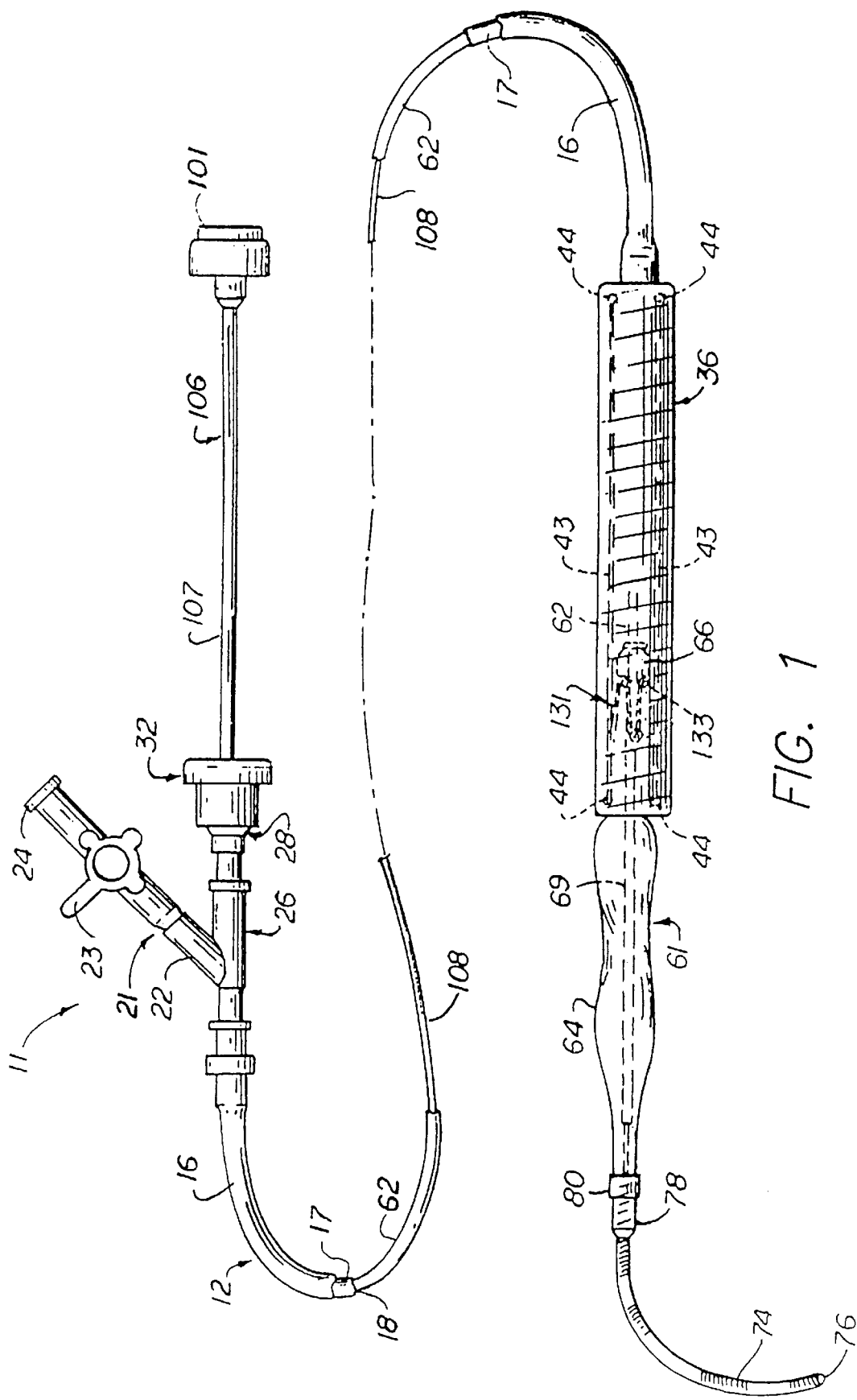
FIG. 1 is an isometric view of an endovascular grafting apparatus and system incorporating the present invention.

In general, the endovascular grafting system is comprised of a capsule catheter having a flexible elongate tubular member with proximal and distal extremities and a capsule mounted on the distal extremity of the tubular member. The capsule is generally cylindrical in shape and is formed of a helical wraps of a metal ribbon. Means is provided for bonding said wraps into a unitary capsule while permitting bending of said unitary capsule. A graft is disposed within the capsule. The graft is comprised of a tubular member having proximal and distal ends. Hook-like attachment means is secured to the proximal and distal ends of the tubular member and face in a direction outwardly towards the inner wall of the capsule. Push rod means is disposed within the capsule catheter and engages the graft whereby upon relative movement between the push rod means and the capsule catheter, the graft can be forced out of the capsule.

More in particular, the endovascular grafting apparatus and system 11 and the devices for use therein are shown in FIGS. 1–10. This apparatus and system 11 includes a capsule catheter 12 (see FIG. 2) which consists of a flexible elongate tubular member 16 formed of a suitable plastic material such as Nylon of a suitable length as, for example, 40 to 100 centimeters and preferably approximately 43 centimeters for the abdominal aortic artery and approximately 70 centimeters for the thoracic aortic artery. The tubular member 16 can have a suitable size such as an outside diameter of 0.187 inches and an inside diameter of 0.125 inches. The tubular member 16 can be produced in a certain color such as blue. In order to make it radiopaque under x-rays, the flexible tubular member 16 is loaded with a suitable radiopaque material such as bismuth subcarbonate or barium sulfate. By way of example, the flexible elongate member 16 can be compounded with approximately 20% of the radiopaque material by weight.

An inner liner 17 is mounted within the tubular member 16. The liner 17 is sized so that it will fit within the tubular member 16. The liner is preferably formed of a lubricous material such as Tefzel (ethylene tetrafluoroethylene) or Teflon FEP (fluorinated ethylene polypropylene). It can have an inside diameter of 0.085 inches and an outside diameter of 0.125 inches and a length as, for example, 41 centimeters which is slightly less than that of the tubular member 16. If desired, the inside diameter of the liner 17 can be in the range of 0.075 to 0.120 inches. The liner 17 is provided with a lumen 18 which extends the length thereof. The liner 17 reduces the inside diameter of the lumen 18 for a purpose hereinafter described. The liner 17 is made of a radiation stable material so that the catheter can be radiation sterilized. Tefzel, or Teflon FEP, which is a polymer is such a radiation sterilizable material. The inner liner 17 also serves to provide additional columnar strength to the catheter 12.

A wye adapter 21 is secured to the proximal extremity of the flexible tubular member 16. The side arm 22 of the adapter 21 has a stop cock 23 mounted therein which is movable between open and closed positions. The stop cock 23 is provided with a Luer fitting 24 which is adapted to be secured to a syringe which can be utilized for injecting a dye, or medications such as a vasodilator.

Figure 2:
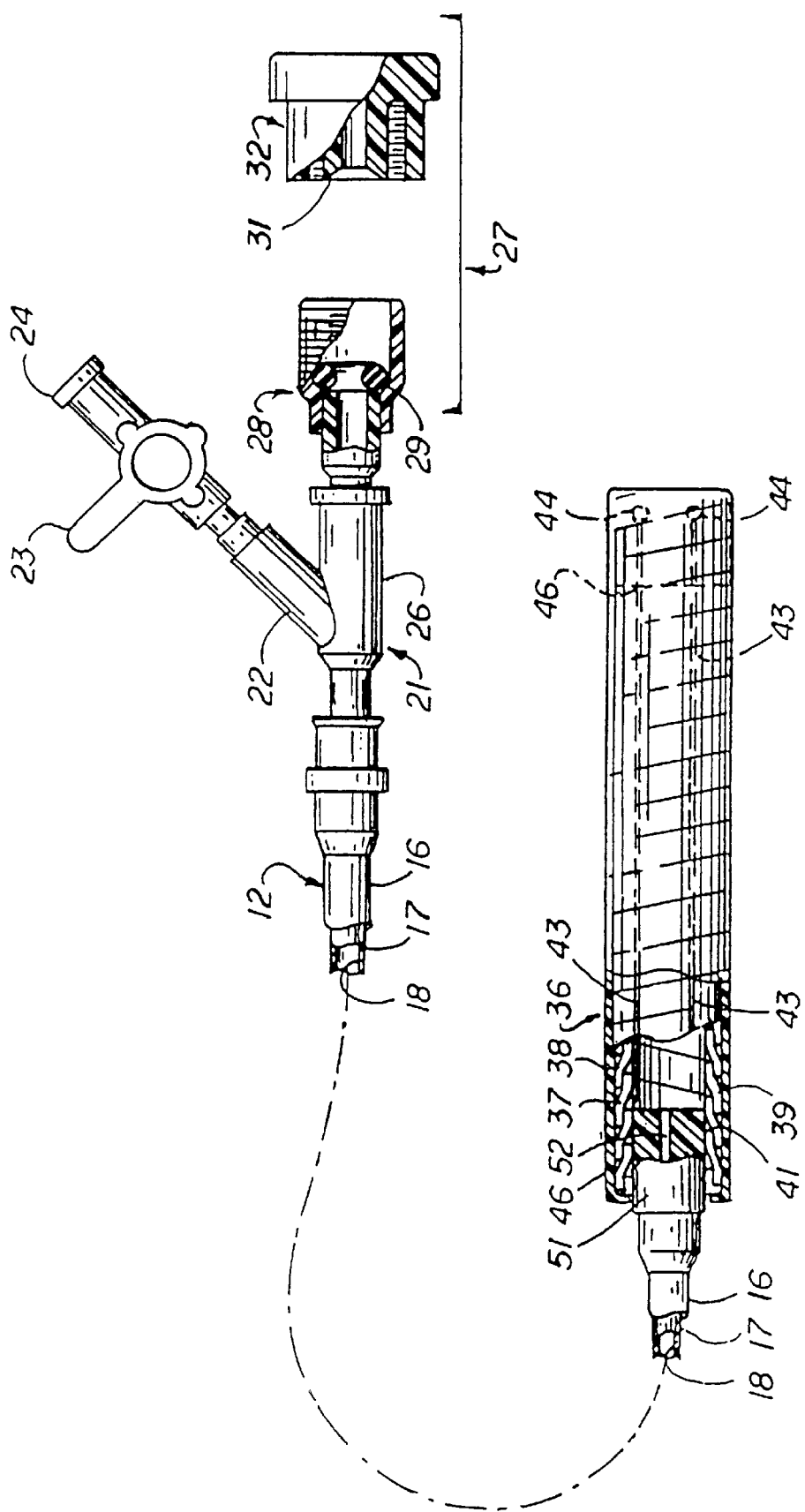
FIG. 2 is a side elevational view partially in cross section of a capable catheter incorporating the present invention.

As shown in FIG. 2 with continued reference to FIG. 1, central arm 26 of the adapter 21 is connected to a Touhy Borst adapter 27 and includes a female part 28 that carries an O-ring 29 which is adapted to be engaged by a protrusion 31 forming a part of the male part 32.

The capsule catheter 12 has a capsule 36 incorporating the present invention mounted on the distal extremity of the flexible elongate tubular member 16. The capsule 36 when used in humans has a diameter ranging from 4 to 8 millimeters. The flexible elongate tubular member 16 which also serves as a shaft for advancing the capsule 36 as hereinafter described and should have a diameter which is less than that of the capsule and therefore has an outside diameter ranging from 3 to 7 millimeters.

The capsule 36 is a composite structure and is formed of an inner layer 37 and an outer layer 38. The inner layer 37 is formed of a stainless steel ribbon 39 with the ribbon having a width of 0.150 inches and a thickness ranging from 0.002 to 0.004 inches and preferably approximately 0.003 inches. The ribbon is spiral wound on a mandrel (not shown) so that each wrap of the ribbon overlaps the preceding wrap by approximately 30 to 50% of the width of the ribbon. Viewing the capsule 36 from the left hand end, the ribbon is wrapped in a clockwise or counterclockwise direction so that the edges 41 face distally or in the direction which is toward the right as shown in FIG. 2 for a purpose hereinafter described. By winding the ribbon 37 at high tension, it is possible to deform it over the adjacent wrap which contributes to the flexibility of the capsule and also at the same time makes it possible to provide a capsule having a low profile. The stainless steel for the ribbon 39 can be of any suitable type, however, it has been found that it is desirable to select a stainless steel which can be heat treated. This enables one to wind the capsule with a ribbon in a ductile state and heat treat the capsule after winding to obtain a spring-like temper. One such stainless steel is 17-7 PH supplied by Brown Metals Company of Santa Fe Springs, Calif.

In order to prevent elongation of the capsule 36 and also to prevent one wrap separating from another of the inner layer 37, a plurality of elongate flexible strands 43 are provided which extend from one end to the other of the capsule. It has been found that the use of four strands has been sufficient with the strands being spaced apart circumferentially by 90°. The strands 43 can be formed of a suitable material such as a Kevlar aramid fiber, 195 denier. These four strands 43 are bonded to the proximal and distal extremities of the capsule by a suitable adhesive such as a cyanoacrylate ester at points 44. The outer layer 38 which overlies the strands 43 and the wrapped ribbon inner layer 37 is in the form of a jacket formed of a suitable material such as heat shrinkable polyethylene. This jacket can have a wall thickness ranging from 0.001 to 0.006 inches and preferably a thickness of approximately 0.004 inches. The polyethylene jacket which forms the outer layer 38 serves to contain the Kevlar strands 43 in close proximity to the inner layers 37 and also serves to prevent elongation of the capsule 36 while permitting the capsule to bend during use as hereinafter described. The outer layer or jacket 38 serves also to provide a smooth surface for the exterior of the capsule 36 by enclosing the edges 41 of the wraps of ribbon 39. In addition, the proximal and distal extremities of the capsule 36 are bonded together by a solder in the regions 46 as indicated in FIG. 2. The solder can be of a suitable type, such as a tin silver solder comprised of 95% tin and 5% silver. When constructed in this manner, the capsule 36 can have an inside diameter of 0.175 inches to 0.300 inches with a nominal wall thickness of 0.0012 inches.

The capsule 36 is secured to the distal extremity of the flexible elongate tubular member 16 by a capsule adapter 51 of a suitable material such as a polycarbonate. The capsule adapter 51 is secured in the proximal extremity of the capsule 36 by suitable means, as a press fit or alternatively, in addition, by the use of a suitable adhesive such as a cyanoacrylate ester. The other extremity of the capsule adapter 51 is also mounted in a suitable manner such as by a cyanoacrylate ester adhesive to the distal extremity of the flexible elongate tubular member 16. The capsule adapter 51 is provided with a hole 52 of a suitable diameter such as 1/16th of an inch.

The capsule 36 made in accordance with the present invention has a number of desirable features. It is particularly desirable because it is flexible and can be bent through an angle of 70 to 120° in a length of 8–20 centimeters. In order to prevent hangups on the inside edges 41 of the ribbon, the inside edges are rounded and polished, preventing damage to capsule contents during ejection as hereinafter described. The Kevlar strands 43, which are also contained by the outer jacket or layer 38, serve to maintain the wrap, prevent stretching or elongation and prevent discontinuities from being formed in the capsule during use of the same. In addition, the Kevlar strands prevent the capsule from being flexed beyond a predetermined angle, as, for example, 120°.

Thus, it can be seen that a capsule 36 has been provided which is very flexible, yet is still very hard and has great strength which inhibits crushing or collapsing while being bent or flexed. In other words, it is kink resistant. It is also puncture proof due to the use of the metal ribbon 37. The capsule 36 is semi-radiopaque and is radiation sterilizable.

As shown in FIG. 3, the endovascular grafting apparatus also includes a balloon catheter assembly 61 which consists of a shaft in the form of a flexible elongate element 62 formed of a suitable material such as irradiated polyethylene tubing extruded to a larger diameter of 0.160 inches outside diameter and 0.090 inches inside diameter and then reduced in size by heating and elongating the same to provide an inside diameter of 0.020 inches and an outside diameter of 0.050 inches. However, the inside diameter can range from 0.015 to 0.025 inches and the outside diameter can range from 0.035 to 0.065 inches for a single lumen balloon catheter assembly. The single balloon inflation lumen 63 extends the length of the catheter. The catheter can have a suitable length as, for example, 50 to 130 centimeters. The lumen 63 can also serve as an injectate lumen and a pusher wire lumen as hereinafter described.

A separate balloon 64 formed of suitable material such as polyethylene is secured to the distal extremity of the flexible elongate member 62 in a manner hereinafter described. A pusher button 66 is provided which is formed of a suitable material such as 300 series stainless steel. The pusher button 66 can have a diameter ranging from 0.120 inches to 0.200 inches and preferably an outside diameter of approximately 0.140 inches. Stainless steel is utilized to achieve radiopacity.

The pusher button 66 is mounted on a fixed position on the catheter shaft 62 and is spaced a predetermined distance from the proximal extremity of the balloon 64 as, for example, a distance of 2 to 3 centimeters. The pusher button 66 is retained in this position longitudinally of the shaft 62 by annular bulbs 67 and 68 which are formed by localized heating in those areas of the shaft 62 which causes it to expand radially in an attempt to achieve its original size to trap the pusher button 66 in that position to the shaft 62. Thus, it can be seen that the pusher button 66 can be mechanically trapped in place without the use of an adhesive and without changing the size of the lumen 63 which extends therethrough.

An alternative embodiment in which the pusher button 66 is movable between the proximal extremity of the balloon 64 and a single bulb 67 is shown in FIG. 4.

A small stainless steel tube 69 is disposed within the balloon 64 and has its proximal extremity seated within the distal extremity of the shaft or flexible elongate member 62. The tube 69 has a suitable inside diameter such as 0.022 inches, an outside diameter of 0.032 inches and a suitable length as, for example, 7.5 centimeters. As can be seen from FIG. 3, the tube 69 extends through the balloon 64 and terminates in the distal extremity of the balloon. The proximal extremity of the tube 69 is flared slightly so that it is firmly retained within the shaft 62 when the proximal extremity of the balloon is fused to the shaft 62 by the use of heat. The tube 69 serves to provide stiffness to the balloon 64 of the balloon catheter assembly 61 and is provided with a lumen 71 extending therethrough through which a fluid such as a gas or liquid can be introduced from the lumen 63 into the lumen 71 to inflate the balloon and to thereafter deflate the balloon 64 by withdrawing the gas or liquid. The balloon 64 can vary in diameter from 12 to 35 millimeters in diameter and can have a wall thickness ranging from 0.001 and 0.005 inches. The polyethylene utilized for the balloon is irradiated to achieve an appropriate balloon size. One balloon made in accordance with the present invention had an outside diameter of 16 millimeters and had a wall thickness of approximately 0.003 inches. In addition, the balloon when deflated is twisted into a helix and heated so as to provide it with a memory which facilitates its introduction into a vessel of a patient as hereinafter described.

A very flexible guide wire 74 is secured to the distal extremity of the balloon 64. The guide wire can have a suitable diameter such as 0.052 inches in outside diameter and can have a suitable length, as for example, 7 centimeters. The guide wire 74 can be a spring formed from wire having a suitable diameter such as 0.009 inches so that it will be radiopaque and thus readily observable under x-rays when being used. The guide wire is provided with a rounded tip 76 which can be formed from a suitable material such as a tin silver solder of 95% tin and 5% silver. The solder tip 76 has bonded therein the distal extremity of a safety ribbon 77 which extends towards the proximal extremity of the spring guide wire 74 and is secured to the proximal extremity thereof by suitable means such as the same tin silver solder hereinbefore described. The guide wire 74 can range in diameter from 0.036 inches to 0.060 inches. The ribbon 77 can be formed of a suitable material such as stainless steel and have a thickness of 0.003 inches and a width of 0.010 inches.

As can be seen from FIG. 3, the proximal extremity of the spring guide wire 74 has been stretched longitudinally beyond the yield point so that there is a space or interstice between each turn of the wire forming the proximal extremity of the spring. A plug 78 of a non-irradiated polyethylene is placed within the proximal extremity of the spring guide wire 74 but remote from the distal extremity of the tube 69. The plug 78 and the distal extremity of the balloon 64 are then heated to cause the non-irradiated polyethylene to melt and flow into the interstices of the stretched spring 74 to bond the spring 74 to the distal extremity of the balloon 64 and to seal the distal extremity of the balloon so that gas cannot escape therefrom.

The guide wire 74 is easily observed using x-rays due to its width and stainless steel composition. Since the pusher button 66 is also formed of stainless steel, it also is an easy marker to follow. The pusher button 66 and guide wire 74 help indicate the position of the balloon 64 because the balloon 64 is positioned between the pusher button 66 and the guide wire 74. The balloon 64 itself can be observed under x-rays because the blood in the patient's vessel is more opaque than the gas used for inflating the balloon. However, increased visibility of the balloon 64 can be obtained by inflating the balloon 64 with a diluted radiopaque contrast solution. In addition, if desired as shown in FIG. 3, two radiopaque bands 79 and 80 of a suitable material such as platinum or a platinum tungsten alloy can be placed on the proximal and distal extremities or necked-down portions of the balloon 64 to aid in ascertaining the position of the balloon 64.

It should be appreciated that although a separate balloon 64 has been provided, if desired, an integral balloon can be provided which is formed of the same tubing from which the flexible elongate tubular member 62 is made. This can be readily accomplished, as is well known to those skilled in the art, by using an additional radiation dose for the balloon region of the tubing.

In FIGS. 5 and 6 there is shown an alternative balloon catheter assembly 81 which utilizes a multi-lumen flexible shaft 82 having a balloon 84 secured to the distal extremity of the same. The flexible shaft 82 is provided with a guide wire lumen 86 of a suitable size, as for example, 0.040 inches which extends the entire length of the shaft and through the balloon 84. It is also provided with a balloon inflation lumen 87 of a smaller size such as 0.010 to 0.015 inches which opens through a notched recess 90 into the interior of the balloon 84. The lumen 87 can be connected to a suitable syringe or other device for inflating and deflating the balloon 84. A pusher button 88 is mounted on the shaft 82 which is held in place by a bulb 89 formed on the shaft 82. A conventional guide wire 91 can then be inserted into the lumen 86 of the catheter assembly 81 and utilized in a conventional manner to advance the balloon catheter into tortuous vessels. Thus it can be seen that applicants' balloon catheter assembly 61 can be utilized in an over-the-wire system which is commonly used in angioplasty. The proximal and distal extremities of the balloon 84 can be fused by heat to the shaft 82 so that the balloon 84 can be inflated and deflated. With the guide wire 91 removed the lumen 86 can be used as an injectate lumen.

Figure 7:
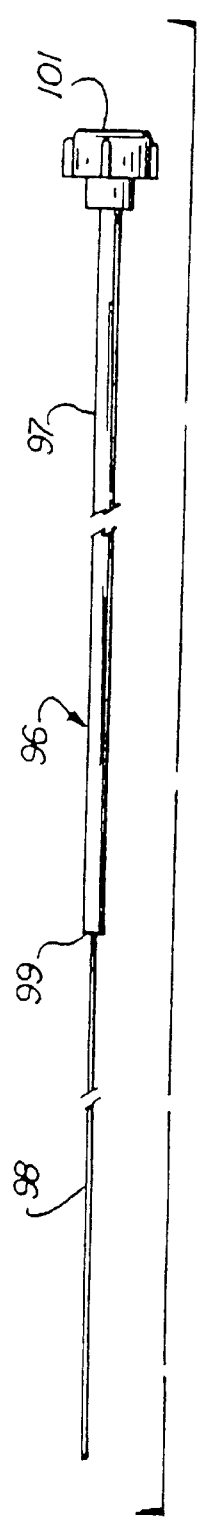
FIG. 7 is a side elevational view partially in cross section of a pusher rod assembly incorporating the present invention.

The endovascular grafting apparatus also includes a pusher rod assembly 96 which is shown in FIG. 7. It consists of a rigid thin wall tube 97 formed of a suitable material such as stainless steel. It has a suitable length as, for example, 21 centimeters and has an outside diameter of 0.065 inches and an inside diameter of 0.053 inches. An elongate solid flexible wire 98 of a suitable diameter as, for example, 0.018 inches is provided which extends centrally into the bore 99 of the tube for the entire length of the rigid tube 97. The wire 98 is secured by suitable means such as an adhesive into a male Luer cap 101 mounted on the proximal end of the tube 97.

Reference is made to FIGS. 1, 3 and 4 with continued reference to FIG. 7. The outside of the tube 97 is small enough so that it can slide inside the lumen sleeve 18 of the liner 17 of the catheter 12. The bore 99 of the rigid tube 97 is large enough so that it can receive the balloon catheter shaft 62 with the wire 98 extending into the lumen 63 of the shaft 62. The wire 98 is long enough so that it can extend through the balloon shaft 62 and through the balloon 64 and the tube 69 to engage the plug 78 provided at the distal extremity of the balloon 64. Typically, the pusher rod assembly 96 has a total length of approximately 75 centimeters.

Figure 8:
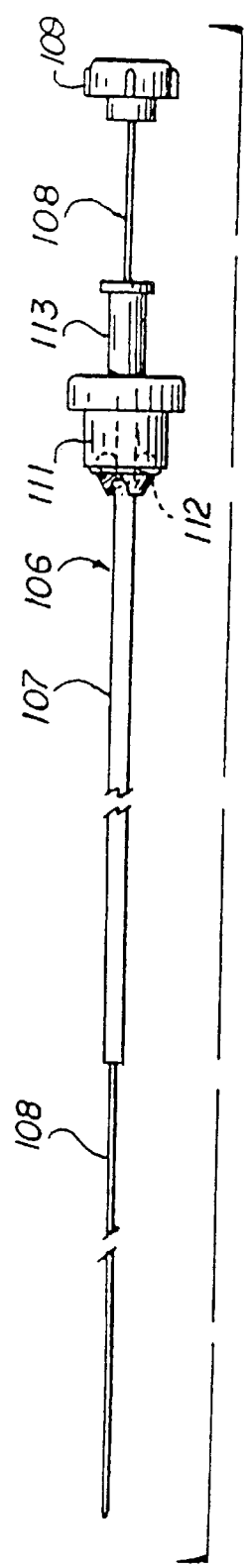
FIG. 8 is a side elevational view partially in cross section of another embodiment of a pusher rod assembly incorporating the present invention.

An alternative pusher rod assembly 106 is shown in FIG. 8 with additional reference to FIG. 1 and consists of a rigid tube 107 similar to the tube 97 with a 0.018 wire 108 extending into the same and being connected to a male Luer cap 109. A Touhy Borst O-ring adapter 111 is secured to the proximal extremity of the tube 107 and is provided with an O-ring 112. A female Luer fitting 113 is mounted on the Touhy Borst adapter 111. In use of the pusher rod assembly 106, the shaft 62 of the balloon catheter assembly 61 is threaded into the tube 106 over the wire 108 and through the O-ring 112. The proximal extremity of the shaft 62 is flared slightly over the O-ring after which the Touhy Borst adapter 111 can be tightened to seal the O-ring 112 around the balloon catheter shaft 62. After certain operations are accomplished as hereinafter described, the male Luer cap 109 and the wire 108 attached thereto can be removed and a syringe (not shown) can be placed on a female Luer adapter 113 to inflate the balloon.

Figure 9:
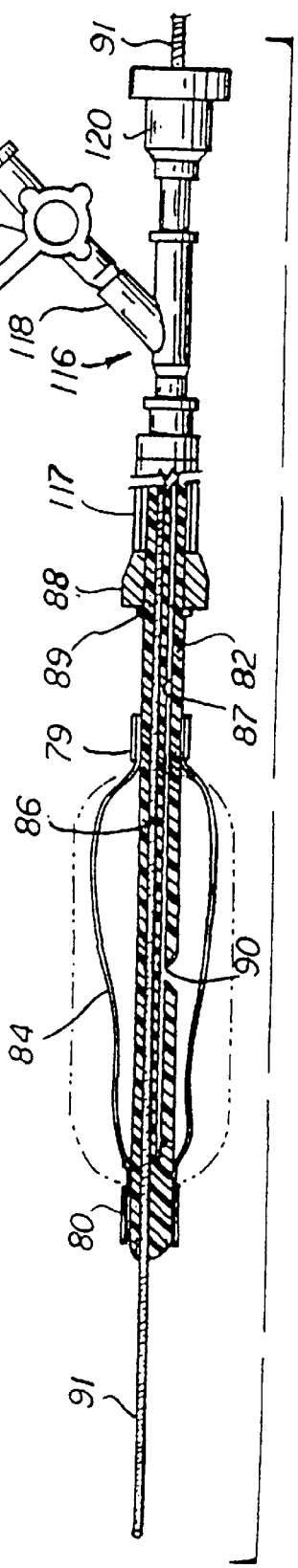
FIG. 9 is a cross sectional view partially in cross section showing in combination a balloon catheter and a pusher rod assembly and a movable guide wire.

An alternative embodiment of a pusher rod assembly 116 cooperating with the balloon catheter assembly 81 shown in FIG. 5 is shown in FIG. 9. The pusher rod assembly 116 is comprised of a flexible relatively rigid tubular sleeve 117 of stainless steel which has a bore of a diameter to accommodate the shaft 82 of the catheter assembly 81 through which the guide wire 91 extends. A wye adapter 118 is secured to the proximal extremity of the sleeve 117. A stop 119 is mounted in the side arm of the adapter 118 and a Touhy Borst adapter 120 is mounted in the central arm of the adapter 118. The guide wire 91 extends through the guide wire lumen 86 and through the wye adapter 118 and the Touhy Borst adapter 120 so that it can be readily engaged by the hand for advancing and retracting the guide wire 91. The balloon 84 can be inflated and deflated through the stop cock 119. By pushing on the adapter 118 a force is applied to the pusher button 88 by the coaxial sleeve 117 for a purpose hereinafter described.

The endovascular grafting apparatus 11 also includes an expandable intraluminal vascular graft 121 shown in FIGS. 10 and 11 for implanting in a body vessel. The graft 121 consists of a deformable tubular member 122 which is provided with first and second ends 123 and 124 and a cylindrical or continuous wall 126 extending between the first and second ends 123 and 124. The continuous wall 126 can be woven of any surgical implantable material such as a Dacron-type 56 fiber. One material found to be satisfactory is DeBakey soft woven Dacron vascular prosthesis (uncrimped) sold by USCI. In order to prevent unraveling of the woven material at the ends, the ends can be melted with heat to provide a small melted bead of Dacron on each end. The tubular member 122 can have a suitable length as, for example, 8 to 15 centimeters with 10 centimeters being typical. The tubular member 122 can have a maximum expandable diameter ranging from 14 to 30 millimeters and a minimum diameter in a collapsed condition of 0.175 to 0.300 inches. Expandable spring means 131 is provided on each of the first and second ends 123 and 124 of the tubular member 122 and is secured to the tubular member. The spring means serves to yieldably urge the tubular member 122 from a first compressed or collapsed position to a second expanded position. The spring means 131 is formed of a plurality of vees 132 with the apices 133 of the vees 132 being formed with helical coil springs 136 to yieldably urge the legs 137 and 138 of each of the vees 132 outwardly at a direction at right angles to the plane in which each of the vees lie. The spring means 131 is shown more in detail in FIG. 11 and as shown therein, the spring means is comprised of a single piece of wire which is formed to provide the vees 132 and also to define the helical coil springs 136 between the legs 137 and 138. In the construction shown in FIG. 10, it can be seen that the spring means 131 have apices lying in three longitudinally spaced-apart parallel planes 141, 142 and 143 which are spaced with respect to the longitudinal axis of the tubular member 122. The two ends of the single piece of wire can be welded together in one of the legs 137 and 138 to provide a continuous spring means.

The spring means 131 is secured to the first and second ends 123 and 124 of the tubular member by suitable means such as Dacron polyester suture material 146 which is utilized for sewing the spring means onto the tubular member. This can be accomplished by a sewing operation with the suture material 146 extending into and out of the wall 126 of the tubular member and in which knots 147 are formed on each of the legs or struts 137 and 138 in such a manner so that the apices lying in the plane 141 extend outwardly and are spaced from the end on which they are mounted and in which the apices lying in the plane 142 extend just beyond the outer edge of the tubular member and in which the apices in the third plane are positioned inwardly from the outer edge.

Hook-like elements 151 are provided on the apices lying in planes 141 and 142 and are secured to the vees 132 in the vicinity of the apices by suitable means such as welding. The hook-like elements 151 can have a suitable diameter such as 0.010 to 0.14 inches and a length from 0.5 to 3 millimeters. The hook-like elements are sharpened to provide conical tips. The hook-like elements 151 should have a length which is sufficient for the hook to penetrate into the vessel wall, but not through the vessel wall.

The spring means 131 with the hook-like elements 151 secured thereto are formed of a corrosion resistant material which has good spring and fatigue characteristics. One such material found to be particularly satisfactory is Elgiloy which is a chromium-cobalt-nickel alloy manufactured and sold by Elgiloy of Elgin, Ill. The wire can have a diameter ranging from 0.010 to 0.015 inches in diameter with the smaller diameter wire being utilized for the smaller diameter tubular members as, for example, 12 to 15 millimeters in diameter and the larger tubular members as, for example, those having a 30 millimeter diameter using the larger wire sizes.

It has been found that the spring force created by the helical coils 136 at the apices 133 is largely determined by the diameter of the wire. The greater the diameter of the wire, the greater the spring force applied to the struts or legs 137 and 138 of the vees. Also, the longer the distances are between the apices lying in planes 141 and 142, the smaller the spring force that is applied to the legs or struts 137 and 138. It therefore has been desirable to provide a spacing between the outer extremities of the legs or struts of approximately one centimeter, although small or larger distances may be utilized.

The hook-like elements 151 at the proximal and distal extremities of the graft 121 are angled at suitable angles with respect to longitudinal axis of the tubular member 122. The hook-like elements face towards each other to facilitate holding the graft 121 in place in the vessel of the patient. Thus, the hook-like elements 151 on the proximal extremity 123 are inclined from the longitudinal axis by 55° to 80° and preferably about 65° toward the distal end of the graft 121 in the direction of blood flow. The hook-like elements 151 on the distal end 124 of the graft or implant 121 are inclined from the longitudinal axis by 30° to 90° and preferably 85° in a direction towards the proximal end 123 and opposite the direction of blood flow. The hook-like elements 151 serve as attachment means at each end of the graft 121 and when implanted oppose migration of the graft.

The helical coil springs 136 placed at the nodes or apices 133 of the vees 132 of the spring means 131 serve to facilitate compression of the graft when it is desired to place the same within the capsule 36 as hereinafter described. The compression of the graft is accomplished by deformation of the coil springs 136 within their elastic limits. Placing the nodes or apices 133 in different planes greatly aids in reducing the size to which the graft can be reduced during compression of the same by staggering or offsetting the hooks or hook-like elements 151. This also helps to prevent the hook-like elements from becoming entangled with each other. The natural spring forces of the helical coil springs 136 provided in the apices of the vees serves to expand the graft to its expanded position as soon as the graft is free of the capsule 36 (FIG. 1). By way of example, as shown in the drawings, three apices or nodes can be provided in the plane 141 and three apices or nodes in the plane 142 which are offset longitudinally with respect to the nodes in plane 141 and six nodes in plane 143. The placement of six nodes or apices 133 in the plane 143 does not interfere with the compression of the graft 151 because there are no hook-like elements 151 at these nodes or apices 133 in the plane. For larger diameter grafts, the spring means 131 can be provided with additional apices or nodes 133 to enhance attachment as hereinafter described.

Radiopaque marker means is carried by the graft 121. The radiopaque marker means takes the form of four radiopaque markers 156. The radiopaque markers are made of a suitable material such as a platinum tungsten alloy wire of a suitable diameter such as 0.003 inches which is wound into a spring coil having a diameter of 0.040 inches and having a length of 0.125 inches. These markers 156 are secured to the tubular member 122 by the same suture material 146. Two of the radiopaque markers 156 are located on the tubular member 122 in spaced apart aligned positions longitudinally of and parallel to the longitudinal axis of the tubular member 122 but are adjacent to the apices 133 lying in the planes 143 at the opposite ends 123 and 124 of the graft 121. Thus the markers 156 are spaced a maximum distance apart on the graft but still within the attachment means carried by the graft 121. Another set of two markers is provided on the tubular member 122 spaced 1800 from the first set of two markers along the same longitudinal axis (see FIG. 15). By placing the markers in these positions, it is possible to ascertain the position of the graft 121 and at the same time to ascertain whether or not there has been any twist in the graft between the first and second ends of the graft. In other words when there is no twist in the graft 121 the four markers 156 form four corners of a rectangle. However, if a twist in the graft 121 is present, then the pair of markers 156 at one end of the graft 121 have a different spacing transverse of the longitudinal axis of the graft then the other pair of markers 156 at the other end.

In order to ensure that the graft 121 will not become dislodged after it has been implanted, it may be desirable to provide alternative hook-like elements to ensure that the graft will remain in place after it has been implanted. An alternative hook-like element 161 is shown in FIG. 12 in which each of the hook-like elements 161 has been provided with a barb 162 which extends outwardly from the main body 163 of the hook-like element. Thus by way of example, the main body 163 can be formed of a wire having a suitable diameter such as 0.012 inches with the diameter of the hook-like body in the vicinity of the barb 162 having a suitable diameter such as 0.010 inches. The hook-like element can have a suitable length such as 1.5 millimeters.

Another alternative hook-like element 166 is shown in FIG. 13 which has a body 167 of a suitable diameter such as 0.010 inches with a conical tip 168. Outwardly extending spring-like ribbons 169 having a suitable dimension such as 0.002 inches in thickness and a width of 0.008 inches are secured by suitable means such as welding of the body 167. As shown, the spring-like elements 169 can flare outwardly so that in the event any attempt is made to withdraw or retract the hook-like element, the spring-like ribbons 169 will become firmly imbedded in the tissue to inhibit such removal. It also should be appreciated that other means can be provided on the hook-like elements to inhibit withdrawal of the same from tissue once they have become embedded in the same. Thus, by way of example as shown in FIG. 13, helical or annular serrations 170 can be provided on the hook body to inhibit such withdrawal. In each of the embodiments with the hook-like elements it can be seen that the profile of the hook-like element is kept to a minimum during the time that it is penetrating the tissue.

The endovascular grafting apparatus 11 is shown assembled for use as shown in FIG. 1 typically in the manner it would be packaged for shipment to a hospital or doctor for use. As shown in FIG. 1 and alternatively in FIG. 14, the graft 121 has been compressed or squeezed onto the balloon shaft 62 and is positioned within the capsule 36 with the pusher button 66 being positioned immediately to the rear or proximal to the proximal extremity 123 of the graft 121. In this connection, it should be appreciated that in order to minimize the diameter of the graft to make use of a capsule of minimum diameter, the balloon catheter should be of minimum profile. The balloon shaft 62 is threaded on the wire 98 and extends into the rigid tube 97 of the pusher rod 96 (FIG. 7). The balloon 64 is disposed forwardly or distally of the capsule 36. The wire 98 is in engagement with the plug 78 in the distal extremity of the balloon 64.

When it is desired to perform a procedure utilizing an endovascular grafting apparatus or system 11 of the present invention to perform the method of the present invention, an apparatus is selected which has the appropriate size of graft 121 within the capsule 36. The length and size of the graft 121 is determined by the size of the vessel of the patient in which the aneurysm has occurred. Typically the size of the graft 121 is selected so that it has sufficient length to span approximately one centimeter proximal and one centimeter distal of the aneurysm so that the hook-like elements 151 of the graft can seat within normal tissue of the vessel on both sides of the aneurysm. Thus, the graft should be two centimeters longer than the aneurysm being repaired. The diameter is selected by measuring the vessel in a preimplant procedure by conventional radiographic techniques and then using a graft 121 of the next larger one millimeter size. During the preimplant fluoroscopy procedure, using a conventional pigtail catheter, the locations of the renal arteries are ascertained so that they will not be covered by the graft 121 when it is implanted.

Let it be assumed that the patient on whom the operation is to take place has been prepared in a conventional manner by use of a dilator with a guide wire and a sheath (not shown) to open the femoral artery or vessel of the patient. The apparatus 11 is inserted into the sheath which has previously been placed in the femoral artery of the patient. This insertion can be accomplished without a guide wire, with a guide wire or by the use of a soft sheath previously positioned over a guide wire. With the construction shown in FIG. 3, the balloon 64 with its guide wire 74 followed by the capsule 36 is introduced into the femoral artery and advanced in the femoral artery by the physician grasping the proximal extremity of the capsule catheter 12 and the cap of the pusher rod assembly 106 (FIG. 8). The balloon 64 is twisted into a helix to place it in its helical memory condition to reduce its profile to a minimum. The balloon 64 and the capsule 36 are advanced by the physician into the desired position by use of the guide wire 74. The physician slightly rotates the apparatus 11 in the direction of the balloon twist to maintain the helical twist in the balloon 64 and pushes on the apparatus 11.

Typically a desired position will be within the abdominal aorta with the proximal extremity 123 of the graft 121 and at least one centimeter distal to the lower renal artery. At about the same time, the physician should rotate the capsule catheter 12 to rotate the capsule 36 and the graft therein in order to orient the radiopaque graft markers 156 such that the distance between the pair of markers 156 at each end of the graft 121 is maximized. As soon the capsule 36 is in the desired position, the Touhy Borst O-ring assembly 27 is opened to permit free movement of the pusher rod assembly 96. With the balloon 64 riding well beyond or just distal of the end of the capsule 36, one hand of the physician is used for holding the pusher rod assembly between the pusher rod assembly 96 by engaging the cap 101 and holding the pusher rod stationary and pulling outwardly on the capsule catheter 12 with the other hand to cause relative movement between the pusher rod assembly 96 in the inner liner 17 and the capsule 36. This causes the wire 98 of the pusher rod assembly 96 to engage the plug 78 of the balloon catheter assembly 61. The pusher button 66 carried by the balloon catheter shaft 62 which is in engagement with the proximal extremity of the graft 121 in the region of the nodes 133 in the plane 143 forces the graft 121 out of the capsule 36 as the capsule is withdrawn. As soon as the proximal extremity of the graft has cleared the distal extremity of the capsule the proximal extremity 123 of the graft 121 pops outwardly under the force of the spring means 131 carried by the proximal extremity 123 of the graft 121 and will spring into engagement with the vessel wall 166.

As soon as this has occurred, the pusher rod assembly 96 (FIG. 7) is pulled out of the capsule catheter 12. While the physician uses one hand to hold the capsule catheter 12 stationary, the catheter shaft 62 which is protruding proximally of the capsule catheter 12 is grasped by the other hand and pulled rearwardly to position the proximal extremity of the balloon 64 into the proximal extremity 123 of the graft 121 as shown in FIG. 15. A conventional hand operated syringe and Touhy Borst adapter (not shown) are then taken and attached to the proximal extremity of the balloon catheter shaft 62. The balloon 64 is then expanded by introducing a suitable gas such as carbon dioxide or a dilute radiopaque liquid from the syringe to urge the hook-like elements 151 outwardly to firmly seat within the vessel wall 166.

As soon as this has been accomplished, the capsule catheter 12 is pulled out further with the balloon 64 still inflated until approximately one-half or more of the graft 121 has cleared the capsule 36. Leaving the balloon inflated provides additional security to ensure that the proximally seated graft 121 will not move during retraction of the capsule 36. The balloon 64 is then deflated. The balloon 64 is then retracted further into the graft and reinflated to ensure that a good attachment is made between the hook-like elements 151 carried by the spring means 131 at the proximal extremity 123 of the graft 121. The capsule 36 can then be removed in successive steps and the balloon deflated, retracted and reinflated. The capsule catheter 12 can then be withdrawn completely to the distal portion of the abdominal aorta to permit the distal extremity 124 of the graft 121 to move out completely of the capsule 36 and to permit its distal extremity 124 to spring open and have the hook-like elements 151 move into engagement with the vessel wall 166. Thereafter, the balloon 64 is again deflated. The balloon catheter shaft is then grasped by the physician's hand and pulled rearwardly to center the balloon 64 within the distal extremity 124 of the graft 121. The balloon 64 is reinflated to set the hook-like elements 151 at the distal extremity of the graft into the vessel wall 166. As soon as this has been completed, the balloon 64 is again deflated. The balloon catheter assembly 61 is then removed from the femoral artery.

The entire procedure hereinbefore can be observed under fluoroscopy. The relative positioning of the graft 121 and the balloon 64 can be readily ascertained by the radiopaque attachment means 131, radiopaque markers 156 provided on the graft, and the radiopaque portions of the balloon 64. If any twisting of the graft 121 has occurred between placement of the proximal hook-like elements and the distal hook-like elements, this can be readily ascertained by observing the four markers 156. Adjustments can be made before ejection of the distal extremity 124 by rotation of the capsule catheter 12 to eliminate any twisting which has occurred. In addition, the distance between the pairs of radiopaque markers 156 longitudinal of the axis is measured on the flat plate abdominal x-ray made during the procedure and compared with the known distance between the pairs of markers 156 longitudinal of the axis of the graft 121 ascertained during manufacture of the graft 121. This is done to ascertain whether longitudinal according of the graft 121 has occurred.

Post implant fluoroscopy procedures can be utilized to confirm the proper implantation of the device by the use of a conventional pigtail catheter. Thereafter the sheath can be removed from the femoral artery and the femoral artery closed with conventional suturing techniques. Tissues should begin to grow into the graft within two to four weeks with tissue completely covering the interior side of the graft within six months so that no portion of the graft thereafter would be in communication with the blood circulating in the vessel. This establishes a complete repair of the aneurysm which had occurred.

It is apparent from the foregoing that there has been provided a new and improved endovascular grafting apparatus, system and method for utilizing the same. The construction of the capsule catheter is such that it has sufficient rigidity to ensure easy and ready placement of the capsule carried thereby. The pusher rod assembly which is used therein is constrained in such a manner so that relatively great forces can be applied to the pusher rod assembly even though the pusher wire has only a diameter of 0.018 inches. The tube 69 also serves to provide a confined space for the wire 98 to sit in while a high compressive force is being applied to the wire. The tube 69 prevents the wire from buckling or kinking within the balloon. It also prevents the balloon from collapsing during insertion of the apparatus 11. The capsule 36 which is provided as a part of the catheter assembly is formed of metal which makes it possible to utilize grafts having very sharp hook-like elements without any danger of then penetrating the capsule during the time that the capsule is being introduced into the vessel of the patient. In addition, the capsule since it is flexible and can bend through angles up to approximately 120° in order to readily negotiate the bends which occur in the vessel of the patient. The balloon catheter is made in such a way that the balloon can be readily introduced into the vessel because of the rigid tubular member provided within the balloon while at the same time permitting inflation and deflation of the balloon through the same tubular member. The pusher button 66 is mounted on the balloon catheter in such a manner so that it cannot shift at all in one direction or proximally longitudinally of the balloon catheter. The pusher button 66 also can only move a limited distance towards the balloon 64 until it reaches the balloon 64. In one embodiment shown in FIG. 3 the pusher button 66 cannot move proximally or distally whereas in another embodiment shown in FIG. 4 it cannot move proximally but can move distally. This is an advantage when retracting the proximal extremity of the balloon 64 into the graft 121 for placement of the proximal hook-like elements 151 because the pusher button 66 can slide forwardly or distally of the shaft 62 as the shaft 62 is retracted to bring the proximal extremity with the balloon 64 into the graft 121. Thus the pusher button 66 will not be pulled back into the capsule 36 and catch on the collapsed distal extremity 124 of the graft 121 within the capsule 26. The balloon is also mounted on the distal extremity of the balloon catheter in such a manner so that the balloon cannot leak. The balloon catheter can be provided with either a fixed guide wire, or if desired, a movable guide wire so that an over-the-wire system can be utilized.

The capsule 36 is constructed in such a manner so that it is semi-radiopaque allowing it to be visualized while still permitting observation of the graft within the capsule and the attachment means provided on the graft. The capsule 36 is also constructed in such a manner so that the hooks which are provided on the graft will readily slide in one direction over the wraps or turns of the capsule without hanging up or catching onto the individual wraps of the ribbon forming the capsule.

The graft which is provided with the helical coil springs at each of the nodes is particularly advantageous in that it permits compression of the graft into a very small size without causing permanent deformation of the attachment means. Because of the spring forces provided by the attachment means, it is possible that the grafts can be implanted without the use of an inflatable balloon for forcing the hook-like elements into the tissue of the vessel. However, at the present time, it is still believed to be desirable to utilize the balloon to ensure that the hook-like elements are firmly implanted into the wall of the vessel so as to inhibit migration of the graft within the vessel.

Figure 29:
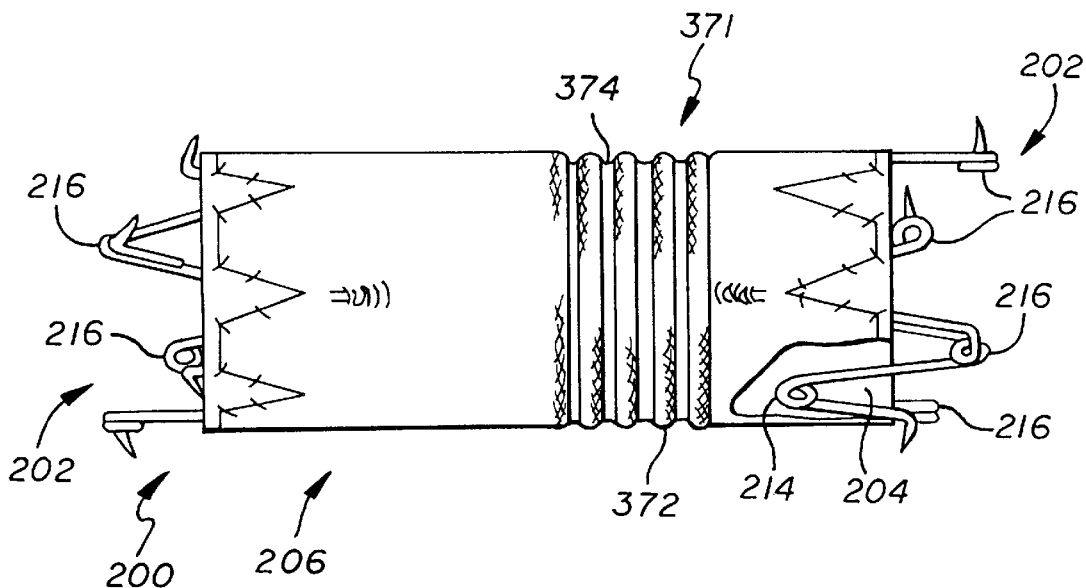
FIG. 29 is a side elevational view of an endovascular graft incorporating an attachment system of the present invention.
Figure 30:
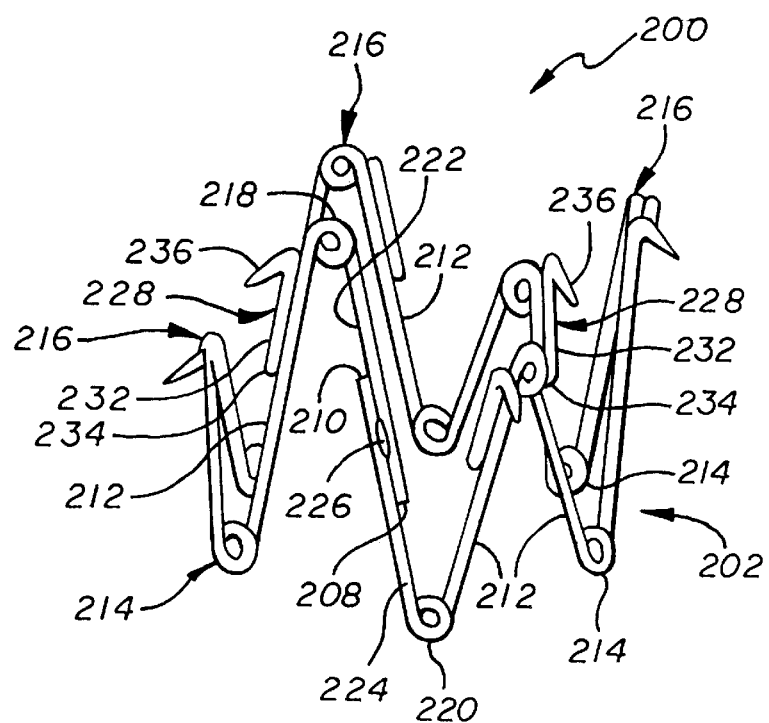
FIG. 30 is an enlarged isometric view showing one of the spring attachment systems shown in the graft of FIG. 29.

As shown in FIG. 30 with reference to FIG. 29, the wire attachment system 200 includes a wire frame 202 and is generally sinusoidal in shape and surrounds the inside 204 of both ends of the graft 206. The wire frame is a single continuous wire with a first end 208 and a second end 210. The wire frame is formed into a sinusoidal shape by bending the wire around a mandrel (not shown) as known by one ordinary skilled in the art. The wire defines alternating base apices 214 that are oriented inside the lumen of the graft. The base apices point generally inward. Alternative protruding apices 216 are formed to point, outward, in the opposite direction of the base apices. The protruding apices generally past the outer extremity of the graft when the wire frame is mounted into the graft.

The terms of reference such as radial, longitudinal, and lateral are defined in spacial relationship to the graft 206. For example, longitudinally outward represents a direction parallel to the axis of the graft outward from the middle of the graft to the end. Terms defining spacial relationships of the attachment system 200 are oriented relative to the graft when the attachment system is mounted into the graft. Thus a longitudinally outward protruding apex 216 is an apex that protrudes longitudinally outward from the graft.

Connecting each alternating apex 214 and 216 are struts 212. The wire frame is made of a stainless spring steel or metal alloy with a high amount of resilience or spring. An example of a preferred wire found to be useful is "ELGILOY" brand cobalt-chromium-nickel alloy manufactured and sold by Elgiloy of Elgin, Ill. The struts are each connected to a protruding apex 216 and a base apex 214. Each apex is connected by a pair of struts that define an angle between such pair of struts.

As illustrated in FIG. 30, the wire frame 202 is formed to have circular continuity that does not destroy the generally sinusoidal shape of the attachment system 200. The term continuity as used herein, defines a wire frame that is affixed end to end so that the frame is one continuous unit. The term circular refers to the fact that the every other apex 214 and 216 is aligned in a generally circular shape.

The sinusoidal shape is retained when there are an equal number of base apices and protruding apices. The apex closest to the first end 208 is a protruding apex and is referred to herein as the first end apex 218. The apex closest to the second end 210 is a base apex and is referred to herein as the second end apex 220. Extending from the first apex to the first end is a first partial strut 222. The strut extending from the second apex to the second end is the second partial strut 224. The first and second partial struts are aligned but point in opposite directions. The length of the first and second partial struts are predetermined to permit overlap of the ends and are equal in length so that the portion of the respective struts that overlap are equidistance from the first and second end apices. The first and second partial struts are welded at a point 226 equidistant from the first and second end apices. Once welded together, the first and second partial struts act as a single strut.

The struts 212 and apices, 214 and 216, are biased to create a radially outwardly directed force when the wire frame 202 is affixed to the inner perimeter of the graft 204. This is accomplished by compressing the struts together so that the angle between the struts generally are smaller than attached when the wire frame is permitted to relax to an equilibrium state. By compressing the struts the longitudinal profile of the attachment system decreases and the attachments system can be affixed to the inside of the graft. When affixed to the graft, the attachment system can relax and expand radially outward to bias the sides of the graft against the wall of the vessel.

The attachment system 200 further includes a plurality of lumen piercing members 228 affixed to the struts 212. The lumen piercing members are designed to protrude radially outward from the attachments system to engage the lumen wall of the blood vessel (not shown in FIGS. 27 and 28) and secure the graft 206 in place. The lumen piercing member includes a wire arm 232 (FIG. 16) constructed of stainless steel wire having the same thickness as the wire in the attachment system. The wire arm has a base end 234 that is welded to the strut of the attachment system. The wire arm is formed with a radially outward protruding hook 236 at the opposite end of the base. The hook ends of the wire arm are positioned longitudinally outward from the base end and extends outward past the adjacent protruding apices 216. When affixed to an adjacent strut, the wire arm is preferably aligned parallel to the strut. FIG. 30 illustrates that the lumen piercing members are affixed to every other strut and have a point of weld generally proximal to the outward end of the strut.

Figure 16:
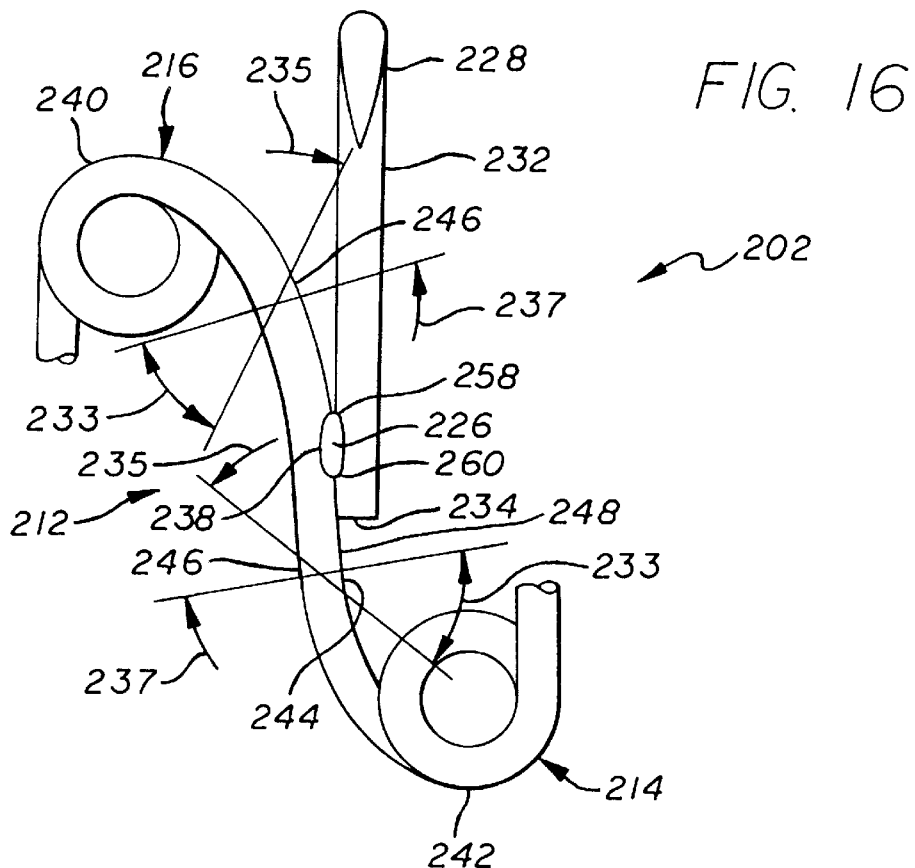
FIG. 16 is an enlarged side elevational view of one strut and lumen engaging member of FIG. 30.

FIG. 16 likewise shows a lumen piercing member 228 attached to a strut 212 adjoining a protruding apex 216 and a base apex 214. However, the base end 234 of the arm 232 is affixed to the strut at a point 238 equidistance from the adjacent protruding apex and base apex. The weld 226 is centered between the top end 240 and bottom end 242 of the strut. The arm of the lumen piercing member is tangential to the strut at the point of the weld. FIG. 16. illustrates how metal fatigue of the welded lumen piercing member can be minimized by locating the weld equidistant from the top and bottom of the strut.

Figure 17:
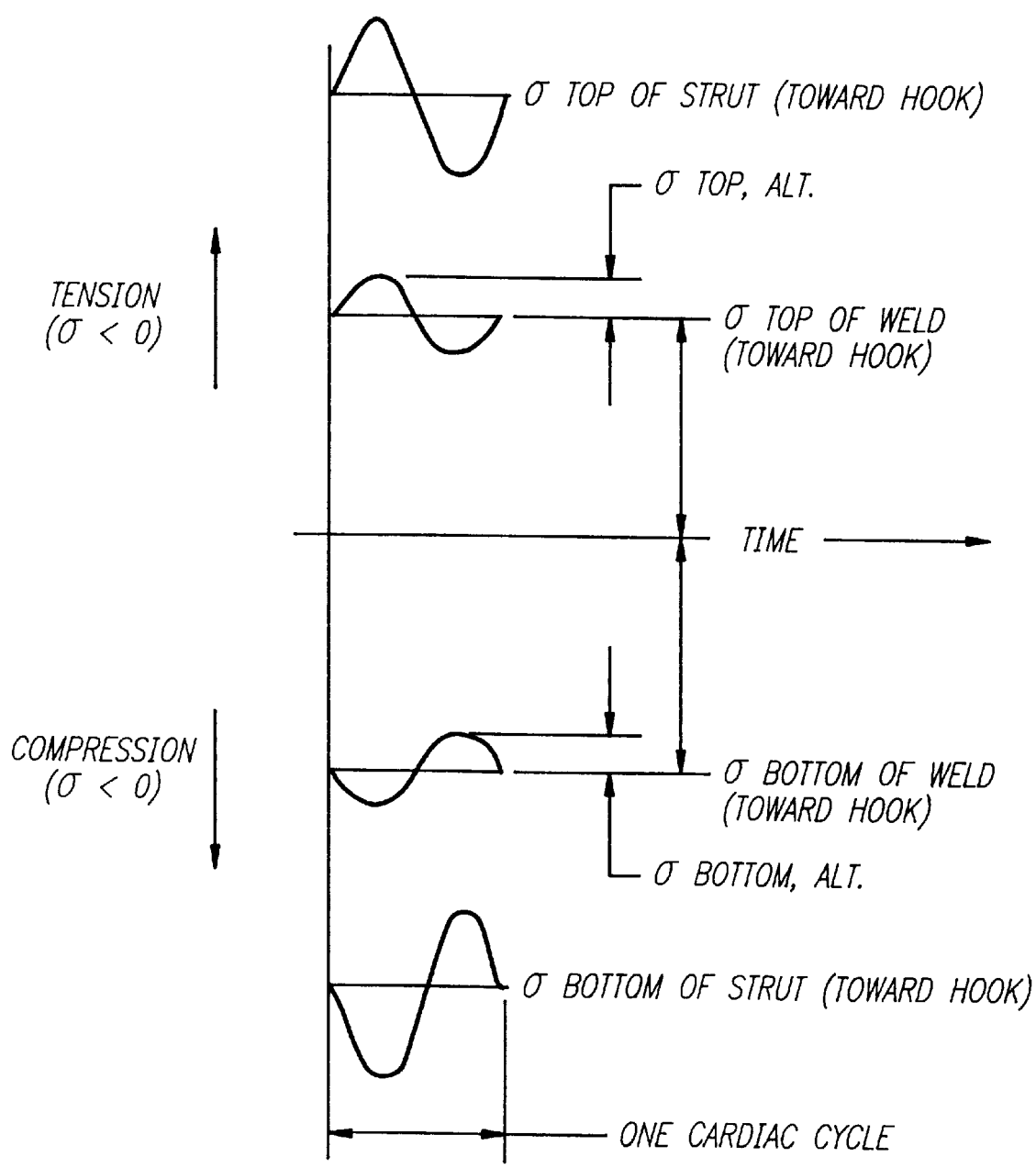
FIG. 17 is a graph showing the compression and tension forces on the strut of FIG. 16.

While the example of FIG. 16 concerns a lumen piercing member 228 welded to a strut 212, the principles described herein apply to any weld in the attachment system including a weld connecting two partial end struts. FIG. 17 illustrates measurement of the compression and tension of the strut at various points along the side of the strut 248 that is welded to the lumen piercing member 228 during a cardiac cycle. Tension is observed when a wire that has resilience and spring is bent from an equilibrium state in an arch.

Compression is observed in the triangular regions represented by numeral 244 at the top and bottom of the strut. Compression is caused when the molecular lattice of the wire is compressed together such that the wire molecules are closer together than if they were in no state of equilibrium. The force arrow 233 indicates the internal repulsion force that biases the wire towards its equilibrium state.

Tension is observed in the triangular regions indicated by reference numeral 246 on the top half and the bottom half of the strut. The tension results when the molecular lattice of the wire is pulled apart from its state of equilibrium. A force internal to the wire in the direction of force arrows 235 and 237 can be observed that biases the wire back to its original position.

FIG. 17 is a graphic representation of the tension or compression of the strut 212 in FIG. 16 during a cardiac cycle. The first curve 250 represents the tension and compression at a point at the top of the strut 240. The second curve 252 represents the tension and compression at the top of the weld 258. The third curve 254 represents the tension and compression at a point at the bottom of the weld 260. The fourth curve 256 represents the tension and compression at the bottom of the strut 242.

With continued reference to FIG. 16 and FIG. 17, the wire frame 202 is in a partially compressed position during the entire cardiac cycle. At least some compression of the wire frame when mounted into a blood vessel lumen is preferred in order to maintain a radial outward force sufficient to hold the graft against the inner wall of the lumen. Since the wire frame is preferably partially compressed at all times throughout the cardiac cycle, a measurable amount of compression and tension will exist at various points along the strut 212. The tension is greatest at the top 240 of a partially compressed strut than any other point along the side 248 of the strut that is welded to the lumen piercing member. At the top of the weld 258, some tension exist, but is considerably less than at the top of the strut. At the bottom of the weld 260, conversely, compression rather than tension exists and has a magnitude approximately equal to the magnitude of tension at the top of the weld. Furthermore at the bottom of the strut 242, the amount of compression of the metal is maximum at the bottom of the strut in an amount proportional to the bottom of the weld.

As the cardiac cycle begins, the blood vessel lumen contracts causing each strut 212 to bend slightly increasing the tension slightly along the top half of the strut and increasing the compression along the bottom half of the strut. Once the compression of the blood vessel reaches a maximum 262, the blood vessel relaxes causing the tension at the top of the strut 240 and the top of the weld 258 to decrease to a minimum. Likewise, the bottom of the strut 242 and the bottom of the weld 260 respond to the relaxation of the blood vessel with a decrease in the amount of compression to a minimum 264. The cardiac cycle becomes complete as the blood vessel again begins to constrict again causing an increase in the tension at the top of the strut and the top of the weld respectively, as well as a decrease in the compression at the bottom of the vessel. Throughout the cardiac cycle, the midpoint 238 defined as the point along the strut that is exactly equidistant between the protruding apex 216 at the top of the strut and the base apex 214 at the bottom of the strut. The compression of the upper portion of the graft and tension of the lower portion of the graft are equal in magnitude at any two given points that are equal distance from the midpoint throughout the entire cardiac cycle. Consequently, the magnitude of compression or tension remains constant absent any compression or tension throughout the cardiac cycle.

Observation of the compression and tension at various points along a strut 212 during the cardiac cycle reveals two important facts. First, the magnitude of compression or tension decreases along the strut toward the midpoint 238. Second, the differential between the magnitude of the maximum and minimum tension or compression during the cardiac cycle decreases along the length of the strut from the respective ends 240 and 242 to the midpoint. From a practical standpoint, the tension and compression contributes to metal fatigue of a wire spring and particularity to a weld 226. Consequently, metal fatigue of the weld is minimized when the weld is located as close to the midpoint of the strut as possible.

Another way of reducing the affect of metal fatigue is to create a wire frame 202 that has no welded parts. FIGS. 18 through 23 illustrate an attachment system for a graft 206 with a lumen diameter of twenty-six millimeters which is a typical size of an aorta. The dimension given below relate to an attachment system 200 for a graft with a lumen diameter of twenty-six (26) millimeters. It shall be apparent to one skilled in the art that the dimensions may be adjusted to fit lumens of different sizes without departing from the spirit of the invention.

To create an attachment system 200 without welds, the welded lumen piercing members 228 illustrated in FIGS. 30 and 16, must be replaced with a lumen piercing member that can be included in the attachment system in such a manner that the lumen piercing members will be responsive to the compression of the spring without welding the lumen piercing members to the wire frame 202. Furthermore, the attachment system must be mounted to the graft 206 so that the wire frame effectively exerts a constant force around the entire periphery of the graft. One embodiment of such an attachment system can be observed in FIGS. 18 through 23.

Figure 18:
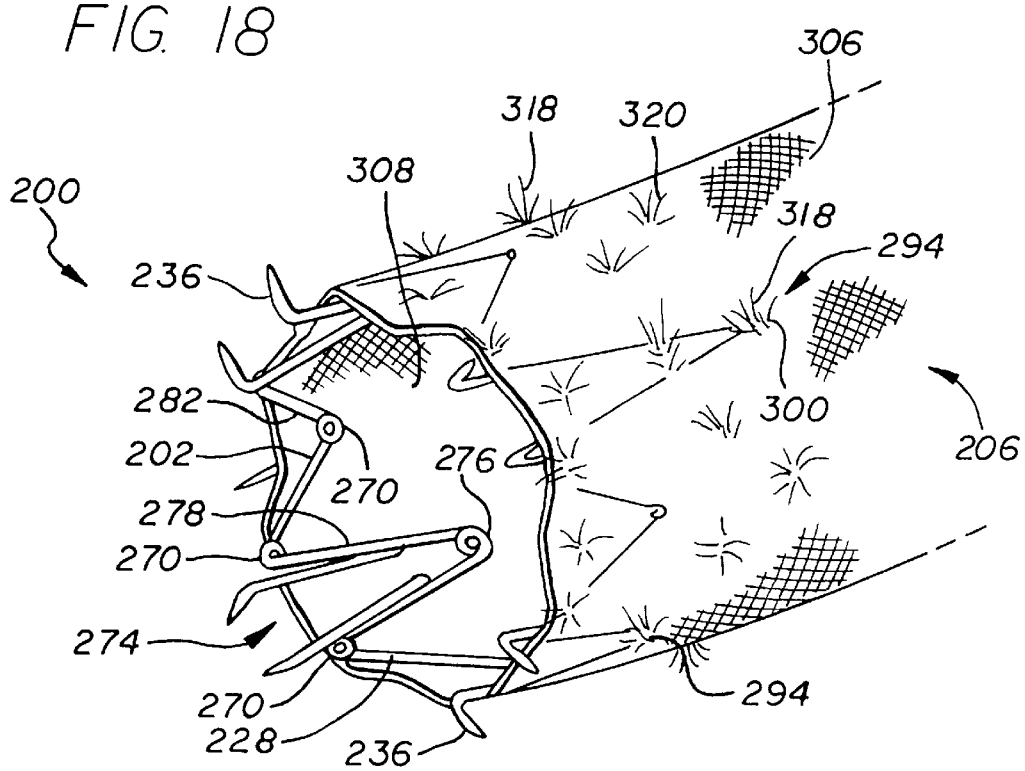
FIG. 18 is an isometric view of an endovascular graft incorporating the attachment system of FIG. 30, further showing the tufts and stitching on the outside and inside of the graft.
Figure 19:
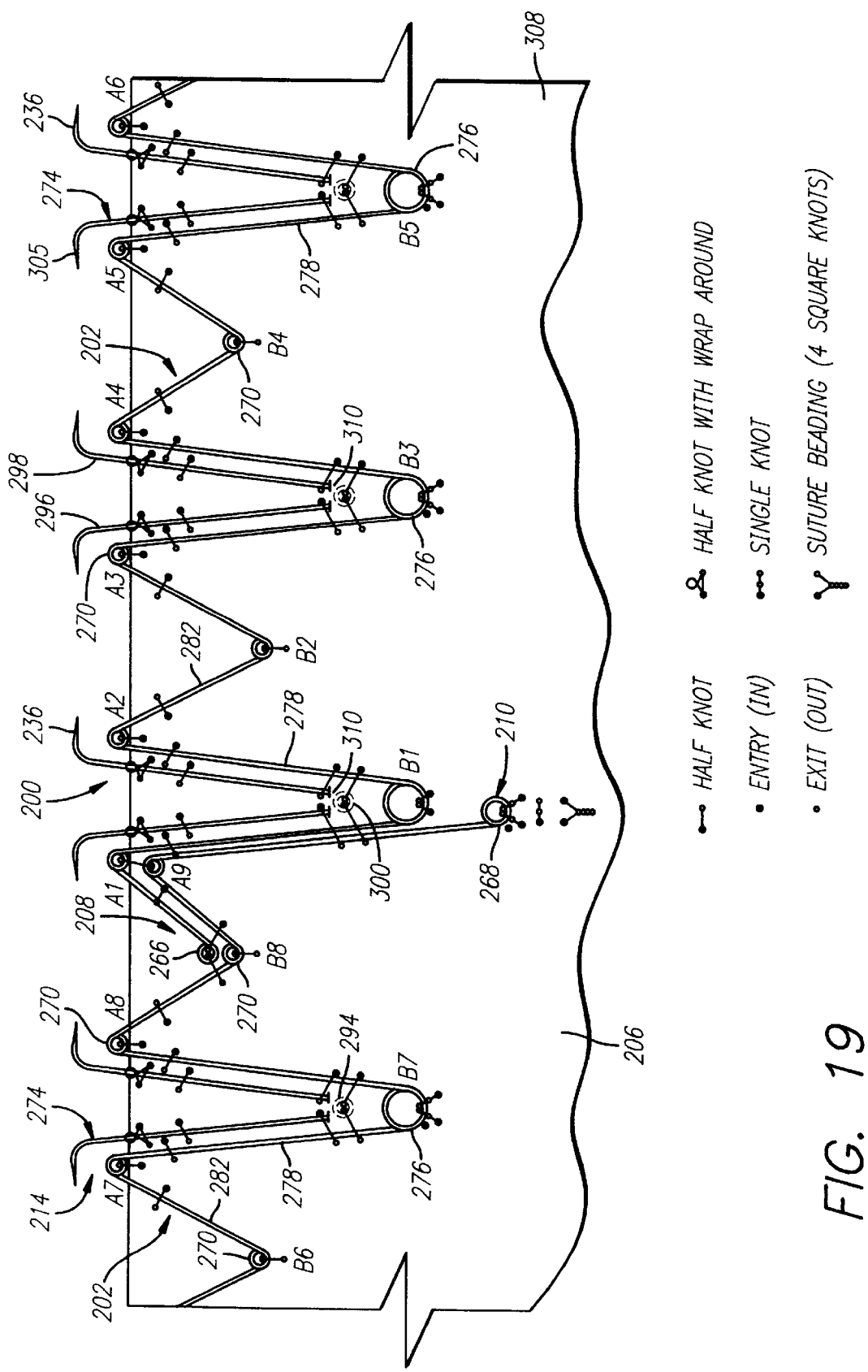
FIG. 19 is a plan view of the inside of an endovascular graft cut longitudinally, showing the wire frame, separate lumen engaging members and stitching of the attachment system.

As shown in FIG. 18 with reference to FIG. 19, the attachment system 200 is configured to affix an end of a tubular graft 206 that may have two or three ends. The graft is generally tubular in shape and is designed to fit into a blood vessel such as the aortic, thoracic, or iliac arteries for repair of an aneurism. The general shape of the wire frame is sinusoidal. The sinusoidal frame has longitudinally inwardly directed base apices that are affixed to the graft longitudinally inward from the outer extremity. Alternatively spaced between the sinusoidal frame are outwardly directed protruding apices A1 through A9 that extend outward from the end of the graft. As shown in the embodiment illustrated in FIG. 19, the wire frame has a first end 208 and a second end 210. The first and second ends of the wire frame are wound into helical coils or helices with one and a half rotations. The helixes on the first and second ends have an inside diameter of 0.031 inches (0.79 mm) and are respectively referred to as first end helix 266 and second end helix 268.

The sinusoidal wire frame 202 is formed with nine outward protruding apices numbered A1 through A9 respectively beginning at the protruding apex A1 closest to the first end helix 266. Each of the apices are wound into a helical spring coil 270. Apex A19 and A9 are respectively the two apices that are closest to the first and second end helices. The alternating base apices are numbered for reference B1 through B8 beginning with the base apices closest to apex A1.

Each of the protruding apices A1 through A9 are integrally connected to adjacent base apices B1 through B8 by struts 212. As observed in FIG. 1A, not all of the struts are of equal length. Rather, the length of the struts are configured to stagger the apices along different planes that are spaced longitudinally apart and are perpendicular to the axis of the tubular graft 206 according to the pattern described below. It is an important objective of the present invention to create a narrow profile for the attachment system 200 when the attachment system is constricted radially. Since the helical apices tend to have a greater radial width than the struts, staggering the apices serves the purpose of creating a narrow profile for insertion into a capsule.

The helixes 270 located at outward protruding apices A1 through A8 are aligned slightly outward from the end of the graft 206. This accomplishes the purpose of minimizing the radial profile of the graft in collapsed position. The graft provides considerable bulk to the attachment system 200 and positioning the apices A1 through A8 beyond the end of the graft distributes longitudinally the bulk of the graft and helices. To further minimize the bulk of radial profile of the attachment system, the struts 212 that are adjacent to apex A9 are shortened slightly to offset apex A9 longitudinally inward from the end of the graft. Consequently, apex A9 when assembled and sewn into the graft is offset longitudinally inward from apex A1 and does not overly the same.

The helixes 270 located at the base apices B1 through B8 as well as the two end helices 266 and 268 respectively are staggered considerably. Apices B1, B3, B5, and B7 are configured with slightly larger diameter helices 276 to accommodate the lumen piercing members 274 which are bent into the shape of a vee. V-shaped lumen piercing members 274 will fit between the struts 278 adjacent to apices B1, B3, B5 and B7 in a close proximal relationship. The lengthened struts that connect the apices are sufficiently long to orient the apices B1, B3, B5 and B7 0.70 inches (17.8 mm) longitudinally inward from the protruding apices. Furthermore, the diameter of the enlarged helices 276 at apices B1, B3, B5, B7 are 0.63 inches (1.2 mm), which is considerably larger than the diameter of remaining smaller helices 282 formed in the wire frame 202. The smaller helices 282 have a diameter of 0.42 inches (1.1 mm). The enlarged helices 276, in combination with the lengthened struts 278, create a space between the struts 278 that extend longitudinally outward from the enlarged helices 276 formed in apices B2, B4, B6 and B8 that conform in shape to the V-shaped lumen piercing members 274 such that the lumen piercing members can fit into the attachment system in close proximity to the lengthened struts and the enlarged helices, without contacting or rubbing against the same.

Apices B2 and B6 may be further staggered with respect to apices B4 and B8. Apices B2 and B6 are oriented 0.46 inches longitudinally inward from the protruding apices. Apices B4 and B8 are oriented 0.36 inches longitudinally inward from the protruding apices. The first end helix 266 is also aligned 0.36 inches from the protruding apices.

Figure 21:
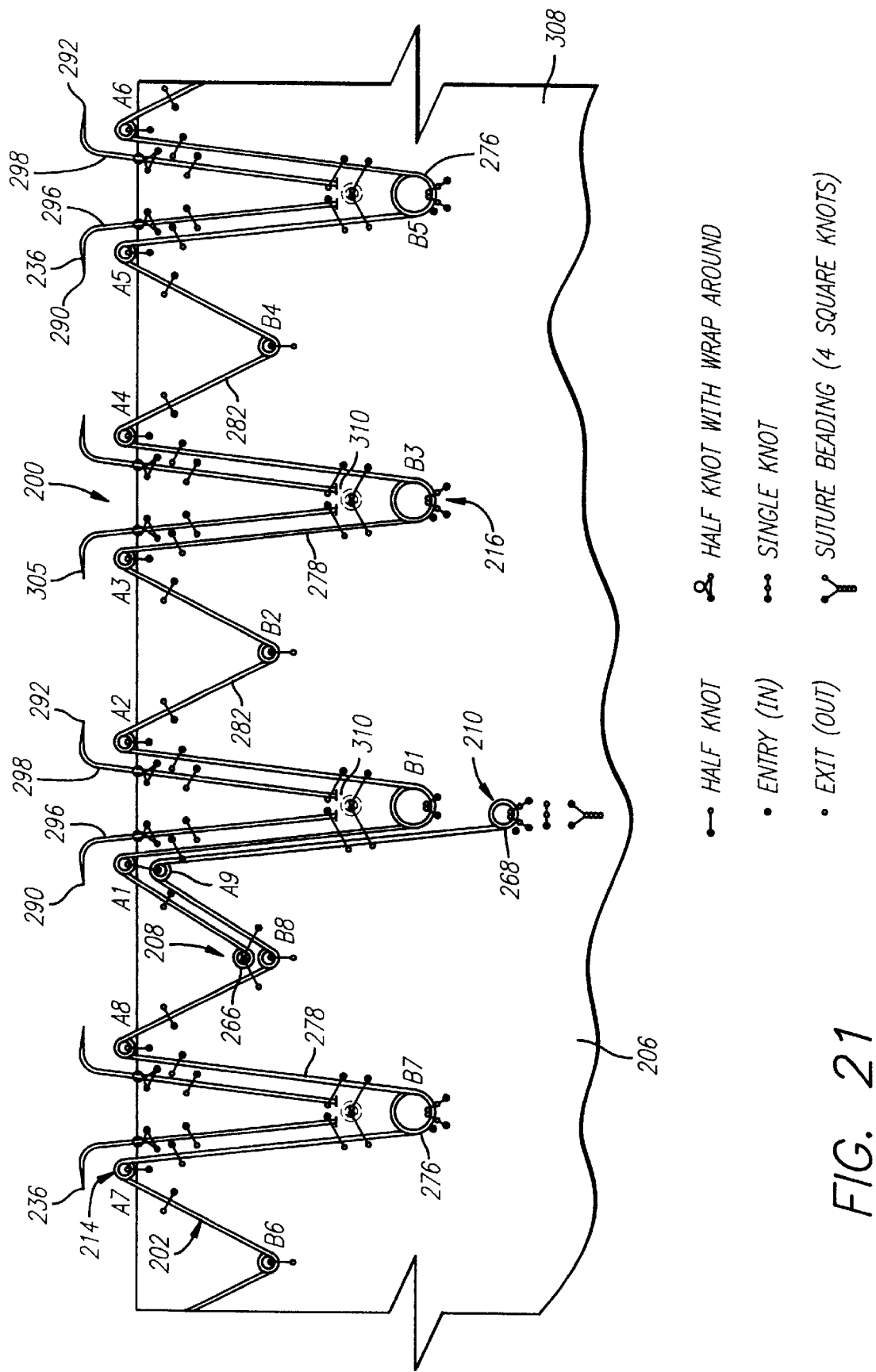
FIG. 21 is a plan view of the inside of an endovascular graft cut longitudinally, showing the wire frame, lumen engaging members and stitching of the attachment system.

As shown in FIG. 21, it may not be necessary or desirable under some circumstances to stagger apices B2 and B6 relative to B4 and B8. For example, the profile of the protruding apices A1 through A8 and the hooks 236 of the attachment system 200 might be sufficiently large that even if the staggering of helices B2 and B6 relative to B4 and B8 occurred it would not serve to reduce the diameter of the overall capsule. When staggering apices B2 and B6 relative to B4 and B8 would not serve to facilitate the use of a narrower capsule or delivery system, then aligning such apices along a fourth plane 288 that may be oriented between 0.36 inches to 0.46 inches longitudinally inward from the first plane 272.

The wire frame 202 of the attachment system 200 illustrated in FIGS. 18 through 21 is designed to fit inside a graft 206 that has a diameter of twenty-six (26) millimeters. When affixing the frame to the tubular graft, the wire frame is preferably partially compressed to maintain a constant outward bias against the wall of the graft. The two ends of the wire frame, 208 and 210, overlap so that the first end helix 266 is aligned longitudinally outward from apex B8. Apex A1 is longitudinally aligned with apex A9. The second end helix 268 is aligned with apex B1 longitudinally inward from apex B1.

The attachment system 200 including the wire frame 202 and the V-shaped lumen piercing members 274 are sutured to the graft 206 at various points throughout the graft. The sewing pattern can best be viewed with reference to FIGS. 19 or 21 showing the stitching from the perspective of the inside of the graft.

Figure 20:
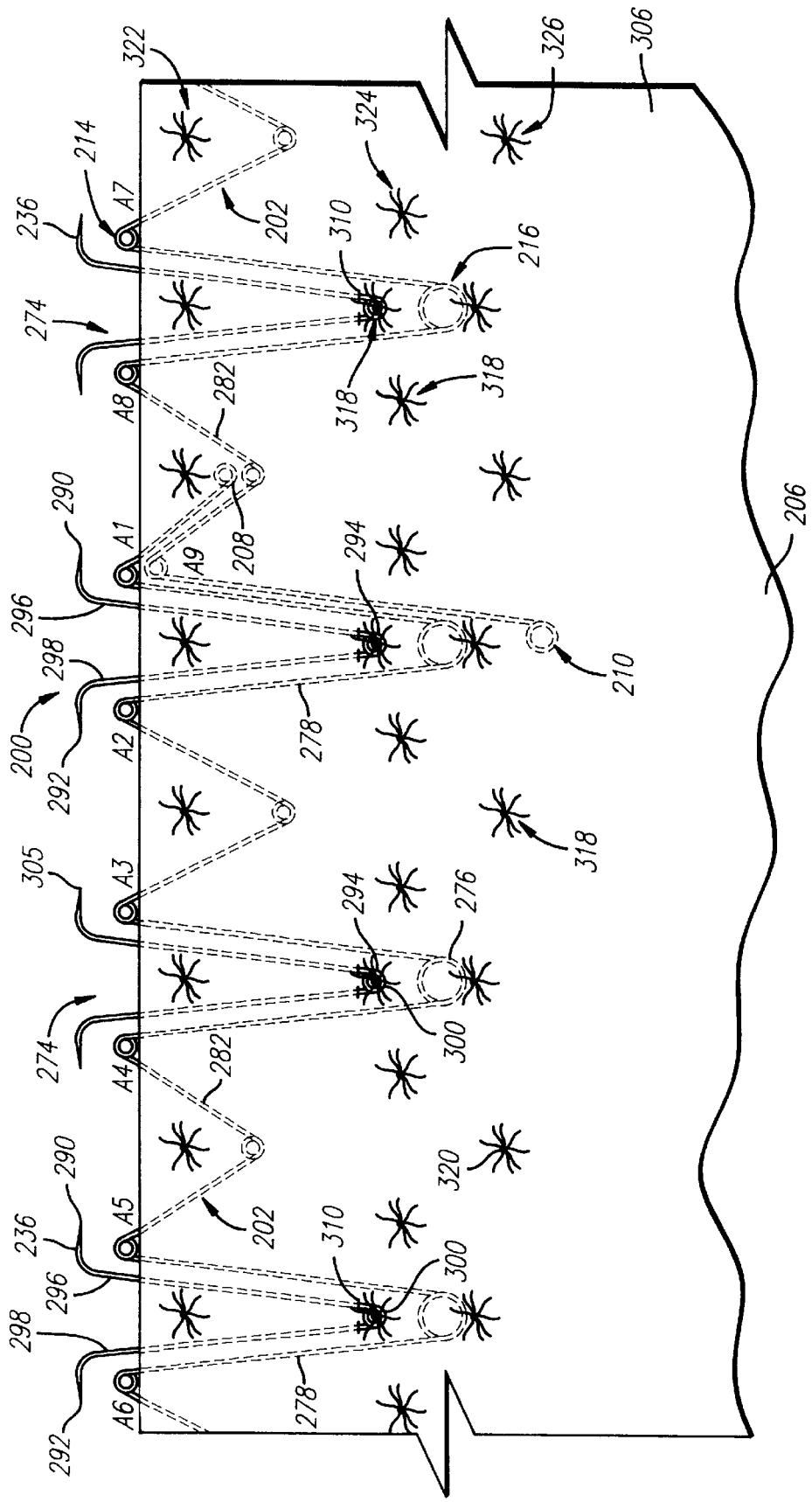
FIG. 20 is a plan view of the outside of an endovascular graft cut longitudinally, showing in partial hidden view the wire frame and the separate lumen engaging members of the attachment system and further showing the tufts attached to the outside of the graft.

In the embodiment illustrated in of FIGS. 18–20, the V-shaped lumen piercing members 274 are not welded to the wire frame 202, but rather are sewn into the graft 206 in close proximity to the sinusoidal wire frame and are responsive to the compression and expansion of the wire frame. To provide stability and flexibility, the lumen piercing members are formed from a single strand of wire with two ends 290 and 292. The wire is bent into a V-shape having an apex 294 and two outwardly protruding arms 296 and 298 that form an acute angle when in relaxed position. The two ends of the wire are bent radially outward to form hooks that, when mounted to the graft, are designed to pierce into the wall of the blood vessel. As shown in FIGS. 19–21, the hooks are shown to point tangential to the graft perimeter. These illustrations are merely to show what the hooks look like. In actuality, the hooks would be directed at an angle perpendicular to the paper. At such an angle, the hooks would be difficult to illustrate.

Figure 31:
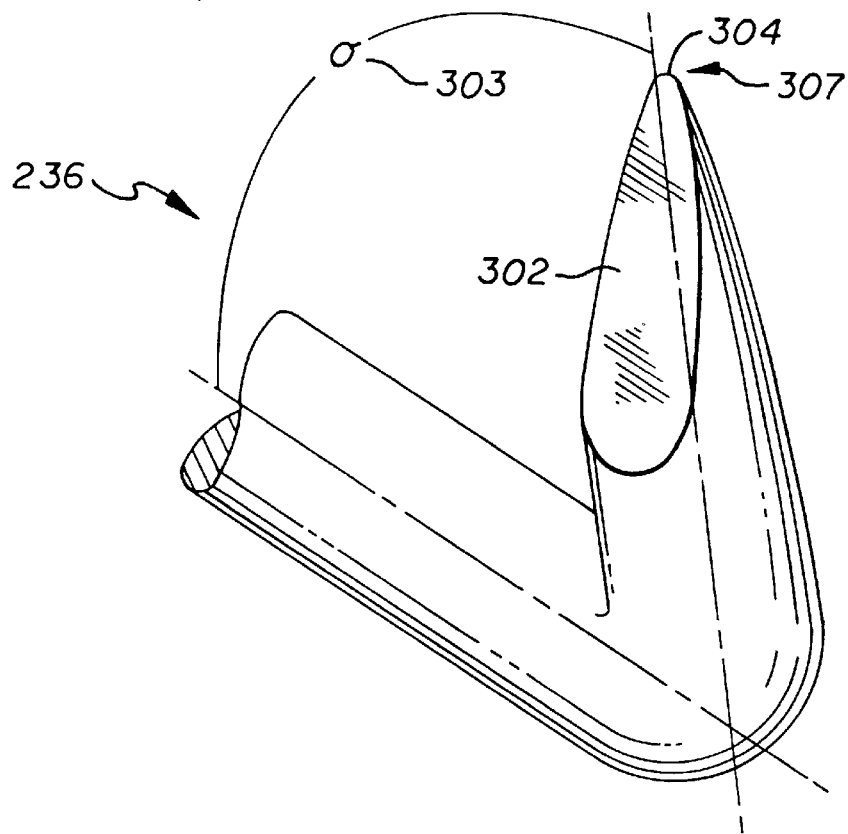
FIG. 31 is an enlarged perspective view of a duckbilled configured hook of a lumen engaging member.

Each hook forms an angle with its respective arm ranging from ninety degrees to forty five degrees, but preferably seventy (70) degrees as shown in FIG. 31 with angle Sigma (σ) 303. The wire of each V-shaped lumen piercing member is wound at the apex to form a helical coil 300. Such a helical coil contributes to the outward bias and spring of the entire attachment system. Absent such a design feature, the V-shaped lumen piercing members would not be as responsive to the contractions of the graft. Moreover, the fatigue life of the hooks are extended because the helical design distributes the tension of the wire over the helix when the arms of the lumen piercing member are subject to continual contractions caused by the pulsing of the blood vessel during the cardiac cycle. The diameter of the apices in the embodiment illustrated in FIG. 19 should have an outside diameter ranging between 0.025 inches and 0.060 inches and preferably 0.047 inches.

There are four pairs of V-shaped lumen piercing members 274 in the embodiment illustrated in FIGS. 19 and 20. The number of V-shaped lumen piercing members mounted depends upon the number of pairs of protruding apices 214 and base 216 apices, discounting the number of apices that overlap at the ends of the wire frame (i.e., apex A1 overlaps with apex A9). The V-shaped lumen piercing members are placed around the graft equally spaced apart. They are fitted into the space between the elongated struts 278 and are mounted adjacent to apices B1, B3, B5, and B7. The arms of the V-shaped lumen piercing members extend parallel to adjacent elongated struts. The V-shaped lumen piercing members of the embodiment illustrated in FIG. 19 has a length of 15–17 mm and a helical diameter of 0.047 inches.

Figure 32:
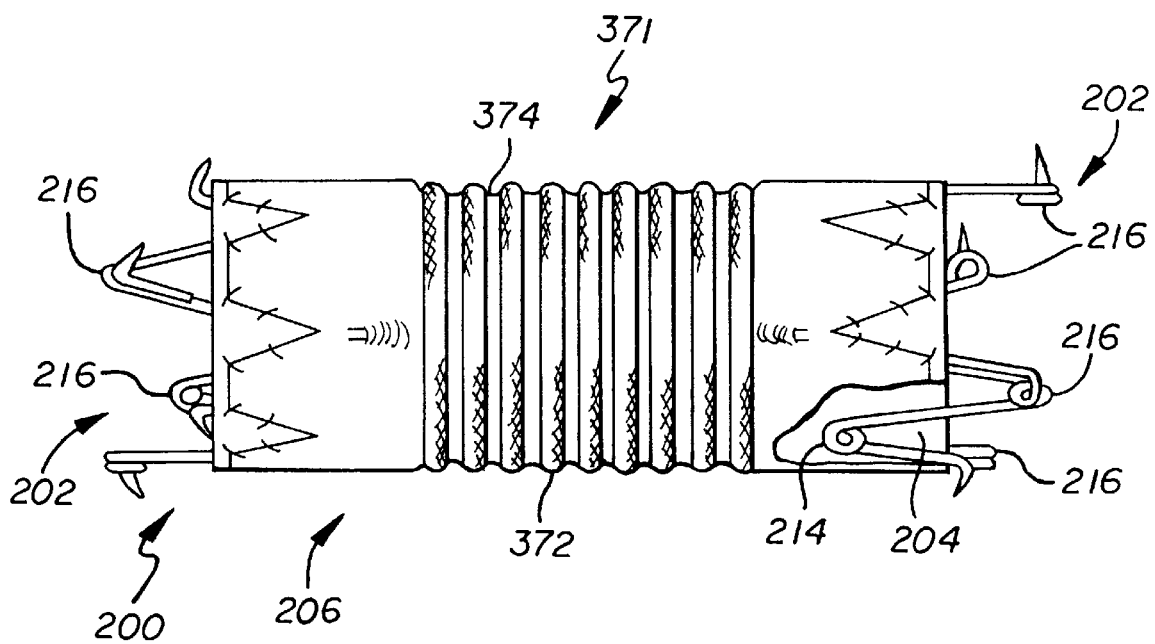
FIG. 32 is an elevational view of an endovascular graft incorporating an attachment system of the present invention.

The hooks 292 have a length of two to three millimeters and are sharpened at the tips 302. The hooks may be sharpened with a conical tip 305 as shown in FIGS. 19 through 21 or with a duck billed tip 307 as shown in FIG. 32. A conical tip is formed when the wire tip is held at an angle against the sharpening tool (not shown) and rotated. The duck bill tip is formed by holding one side of the tip of the hook 292 against the sharpening surface (not shown) at an angle. Not rotating the wire results in an oblong flat surface 302 and a sharpened curved cutting edge 304 that cuts into the blood vessel wall when the hook is pressed against the vessel wall.

One possible method of attaching the V-shaped lumen piercing members 274 to the frame can be observed with reference to FIGS. 19 and 20. As can readily be observed, the helices of the V-shaped lumen piercing members are located on the outside 306 of the graft 206 while the arms 296 and 298 extend parallel to the struts along the inside 308 of the graft 206. By mounting the V-shaped lumen piercing members directly through the fabric of the graft, the V-shaped lumen piercing members will be mounted more firmly. Furthermore, the fabric of the graft separates the helix of the V-shaped lumen piercing member 300 from the respective adjacent enlarged helices 276 and thereby prevents the helices of the V-shaped lumen piercing member from rubbing against the adjacent base helices.

The V-shaped lumen piercing members 274 are mounted into the graft by pressing together the two arms 296 and 298 of the V-shaped lumen piercing members until the hooks are separated by a distance approximately equal to the outer diameter of the helices. The hooks are then punctured through the fibers of the graft from the outside 306 of the graft wall 206 to the inside 308 of the graft 308. The entry holes made by the V-shaped lumen piercing members are spaced longitudinally outward by more than the outer diameter of the helices 300 of the V-shaped lumen piercing members. The spacing apart of helices 300 of the V-shaped lumen piercing members prevents them from radially overlapping the enlarged base helices 276. This longitudinal spacing also furthers the goal of distributing the bulk of the attachment system 300 thereby narrowing the radial profile of the graft 206 when in a compressed state. The apices of the lumen piercing member, prior to insertion of the hooks through the graft, point outward towards the end of the graft. The two hooks should preferably be laterally aligned so that the entry holes 310 through the graft wall created by the hooks are laterally aligned. The V-shaped lumen piercing members are pressed through the puncture holes and slid inward along the arms until the helix 300 contacts the outer wall of the graft. The V-shaped lumen piercing members are inverted to an upright position thereby orienting the hooks radially outward to engage the wall of the blood vessel.

The arms 298 of the V-shaped lumen piercing members 274 are compressed before being sewn to the graft 206 to maintain the outward bias of the graft. The distance between the arms at the edge of the graft is preferably six to seven millimeters. The arms are sutured to the graft parallel to and in close proximal relationship to the struts 278 adjacent to the V-shaped lumen piercing members. The arms of the V-shaped lumen piercing members are generally not sutured directly to the adjacent struts. The arms of the V-shaped lumen piercing members and the adjacent struts are sutured separately in order to prevent them from rubbing together.

Figure 22:
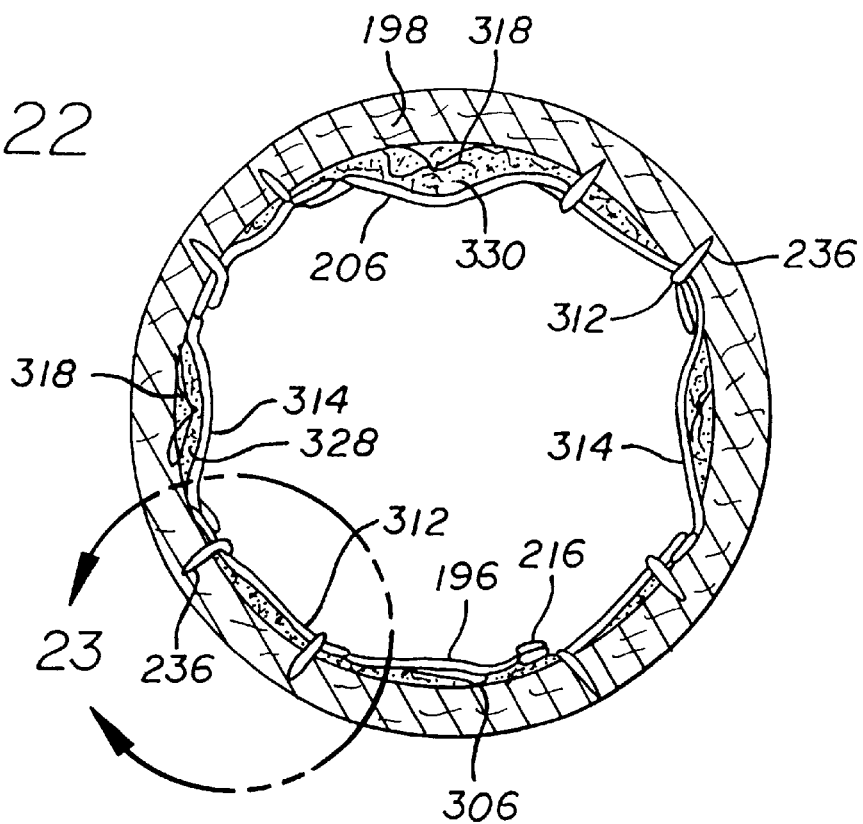
FIG. 22 is a top plan view of an endovascular graft having an attachment system as shown in FIG. 20, showing the pleats and tufts of the graft secured within the vessel lumen.
Figure 23:
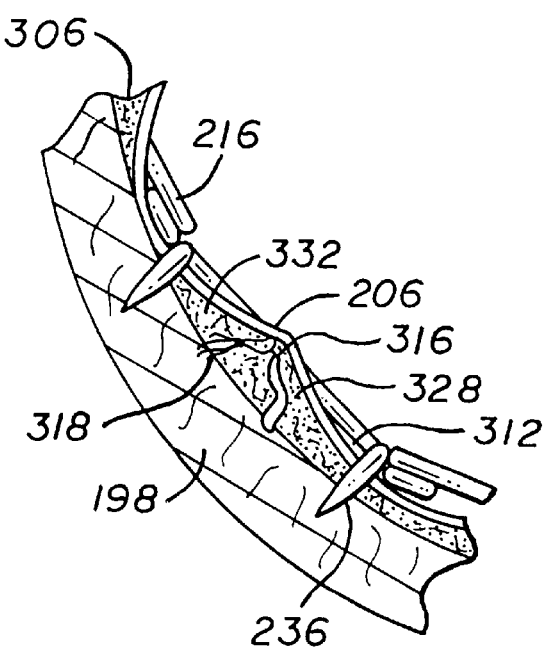
FIG. 23 is an enlarged top plan view of the area shown along curve 23 of FIG. 22.

The attachment system 200 is inserted into a capsule (not shown). When the graft 206 is deployed to the appropriate location by a catheter delivery system (not shown), the graft is removed from the capsule. Immediately upon removal, the attachment system exerts a radially outward force on the wall of the graft biasing the graft against the wall of the vessel 198 (FIGS. 22 and 23). The deployment balloon (now shown) is then used to further force the wall of the graft against the wall of the vessel and to cause the hooks 236 of the attachment system to pierce the vessel wall.

FIG. 22 is the cross section of a blood vessel that has a graft 206 implanted into the wall of the vessel 198. The hooks 236 are implanted into the wall but preferably do not puncture through the wall of the blood vessel. The protruding apices 216 can be observed around the top of the graft 196. The pressed portion of the graft 312 that is directly pressed against the vessel wall by the wire frame 202 forms a seal that assists in the prevention of fluid leaking around the end of the graft. Since the wire frame is continuous, the portion of the graft that is pressed directly against the vessel wall should in most cases be continuous. The relieved portions of the graft 314 are the parts of the graft that are not directly pressed against the wall of the vessel. The relieved portion of the graft are most vulnerable to leaks.

Leaking is also more likely to occur if the vessel is deformed. For example, the graft may have a slightly larger diameter than the inner dimension of the vessel or the vessel wall may not be smooth. In such circumstances, pleats in the graft are sometimes formed between the struts 212. Another factor that increases the likelihood of pleating is the pulsing of the blood vessel during the cardiac cycle as described above. When the blood vessel is contracted, pleating may be mildly accentuated.

The further prevention of leaks can be accomplished by texturing the outside of the graft 306 with a plurality of filaments or fibers that are spun, woven, knotted, pressed or otherwise loosely associated to form a puffed textured filler that can be sewn to or affixed to the outside of the graft proximal to the end of the graft. The filler of the embodiment illustrated in FIG. 18 with reference to FIG. 20 includes stitches of a biocompatible synthetic yarn called tufts 318. The tufts are formed by stitching two or more strands 320 of synthetic yarn into the graft with the ends of the strands pointing outward from the side of the graft. The strands can be formed or knotted by employing a double knot or a square knot. The ends of the strands can be frayed to increase the surface area exposed and to distribute the filaments as much as possible.

A possible pattern of orienting the fibrous tufts 318 includes covering the graft 206 proximal to the perimeter of the attachment system with batting or by sewing loosely spun synthetic yarn such as polyester around the perimeter of the graft. Such a configuration would certainly fill all of the gaps that may arise. However, when considering the competing need of maintaining a narrow profile for the attachment system and graft in order to fit the attachment system into a capsule, the more spatially conservative approach of using tufts may be preferred.

FIG. 20 illustrates an example of a pattern of placing fibrous tufts in a more spatially conservative pattern. The tufts 318 while conserving radial bulk of the graft, cooperate with the attachment system to minimize leakage of blood. As previously stated, the parts of the graft that are most vulnerable to leaks are the relieved portion of the graft 314. Therefore, the tufts will be centered in between such places. For example, a first row 322 of tufts are sewn into the spaces between the protruding apices three to five millimeters longitudinally inward from the end of the graft. The tufts are trimmed to three to five millimeters in length. The ends of the tufts are teased or frayed to spread out the filaments throughout the relieved portion of the graft.

A second and third row of tufts 326 are respectively sewn to the graft 206 near the base apices. The second row of tufts 324 are two to five millimeters longitudinally outward from the base apices B2, B4, B6, and B8. The second row has eight tufts and each tuft is radially aligned with each protruding apex 1-8. The second row of tufts are located three to seven millimeters longitudinally inward from the first row and are radially aligned with each of the eight base apices B1–B8. Each of the tufts in the second and third rows are five to seven millimeter long.

Polyester tufts are knotted directly onto each helix of the V-shaped lumen piercing members which are located on the outside 306 of the graft 206. The polyester tufts are designed to seal the holes in the graft created by puncturing the hooks 236 of the V-shaped lumen piercing member through the wall of the graft as well as provide a surface covering the apex that can bind to tissue growth of the graft.

Referring now to FIG. 22 with continued reference to FIG. 23, the tufts can be observed around the outer surface 306 of the graft 206 between the protruding apices 216. These tufts serve two purposes. First, when a leak occurs, the fiber of the tufts assist in the clotting of the leak. By way of illustration, a pleat 316 is shown between two apices. A tuft 318 is sutured to the graft within the pleat. A space 328 is created between the pleated graft that is vulnerable to leaks. The filaments or strands 320 of the tufts provide a surface to which blood 330 may clot to fill the space and prevent further leaks. A second benefit becomes apparent once the graft has been in place for a considerable period of time and the tissue 332 begins to build up along the wall of blood vessel 198. The tissue growth 332 that builds up to the side of the graft from the blood vessel wall further anchors the ends of the graft 206 to the wall.

Another embodiment of the present invention includes an attachment system that is well adapted to affix a graft into the iliac arteries as illustrated in FIGS. 24 through 28. The wire frame has two wire frame parts 334 and 336 that are bent into a generally sinusoidal shape and are respectively referred to as the first and second wire frames. The first wire frame 334 terminates in a first end 338 and a second end 340. Each frame has four base apices. The base apices of the first frame are numbered D1, D2, D3, and D4 beginning with the apex closest to the first end. The second wire frame also has four base apices numbered D5, D6, D7 and D8 in order beginning with the apex closest to first end 342 of the second frame. Each wire frame has three protruding apices. The and ending with the apex closest to the second end 344 first frame has protruding apices labeled from said first end to said second end respectively, C1, C2, C3. The second wire frame has protruding apices labeled from said first end respectively, C4, C5, and C6.

All of the apices have helical coils 346 with a 0.031 inch diameter. The wire has a 0.010 inches (0.25 mm) diameter for ten to fourteen millimeter grafts and is made of an alloy as described above.

Figure 26:
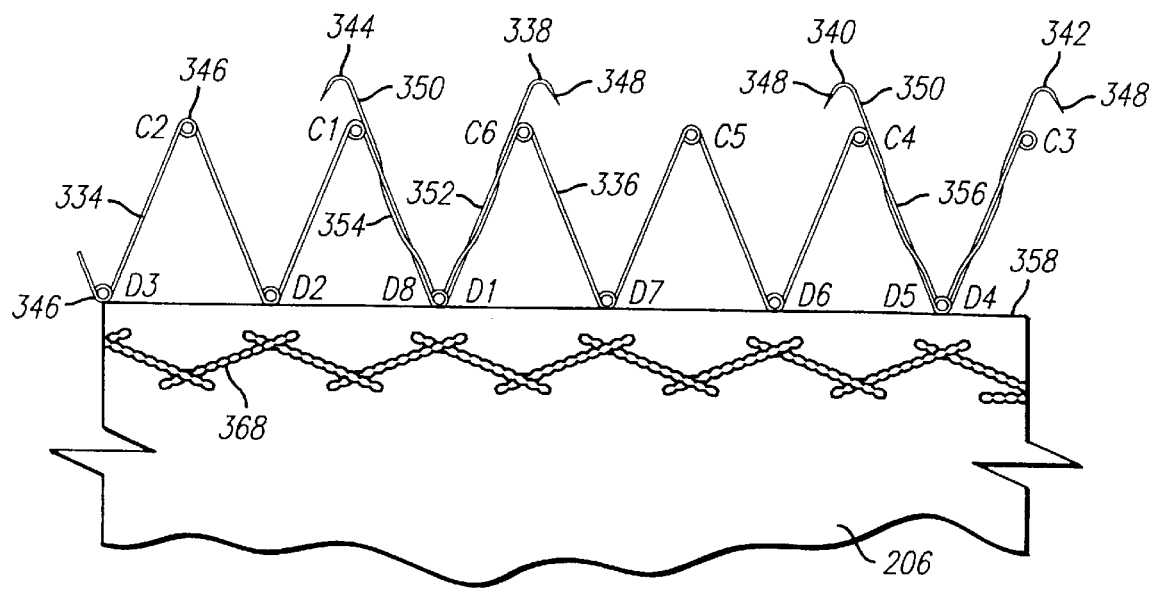
FIG. 26 is a plan view of the graft and attachment system of FIG. 24 cut longitudinally, showing the wire frame of the iliac attachment system having lumen engaging members.

Lumen piercing members 348 extend outward from apices D1 and D4 towards said first end 338 and second end 340 of said first wire frame 334 respectively. Similarly, lumen piercing members extend outward from apices D5 and D8 towards said first end 342 and second end of said second wire frame 336 respectively. Each lumen piercing member has a longitudinally outward protruding arm 350 that is approximately one millimeter in length. At the outermost extremity of the lumen piercing member, the arms are bent in a radially outward direction to form hooks which are designed to pierce the lumen to which the graft is being affixed. While the hooks in FIG. 26 are shown to protrude at a tangent to the circumference of the graft, this representation merely shows the angle of the hooks with the protruding arm 250. The hooks actually protrude radially outward as shown in FIG. 26.

The base apices are preferably sewn to the outer extremity of the graft and are spaced equally around the circumference at six points with two pairs of overlapping base apices. Base apex D1 overlaps with base apex D8 when affixed to the graft. Base apex D5 likewise overlaps apex D4.

An important feature of the present invention is how the two wire frames 334 and 336 can be affixed together to cooperate as a single wire frame unit without actually welding the two frames together. The first and second wire frames are affixed together by wrapping the arm 350 of the lumen piercing member around the adjacent struts 352–258 when oriented with the overlapping base apices above. For example, the lumen piercing member on the first end 338 of the first wire frame is wrapped around the strut 352 extending between base apex D8 and protruding apex C6. The lumen piercing member on the second end of the second wire frame is wrapped around the strut 354 extending between base apex D1 and protruding apex C1. The lumen piercing member on the second end 340 of the first wire frame is wrapped around the strut 356 extending between base apex D5 and protruding apex C4. The lumen piercing member on the first end of the second wire frame is wrapped around the strut 358 extending between base apex D4 and protruding apex C3.

By wrapping around, it is meant that the arm 350 of the lumen piercing member 348 makes at least one full twist around the adjacent strut 352–358. It is desirable that the struts rest against the inside edge of the adjacent protruding apices C1–C6. When the arm, after being twisted around the adjacent strut is radially inward from the protruding apex, the spring tension caused by twisting the wire arms together with adjacent struts 352–358 more forcefully biases the arm outward. In some instances, the arm can be further supported by the protruding apex by threading the arm through the eye of the helix of the protruding apex.

Figure 24:
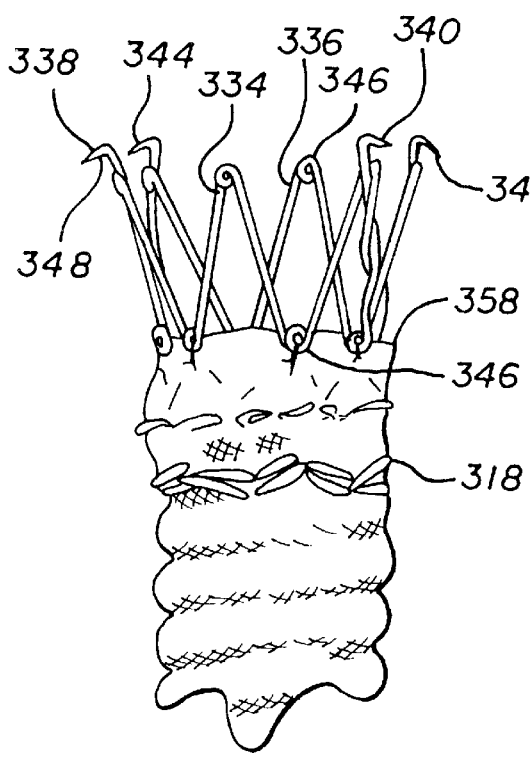
FIG. 24 is a side elevational view of an iliac attachment system, wherein the base apices are sewn to the end edge of a leg of a bifurcated graft.

As shown in FIGS. 24 and 26, the pair of wire frames 334 and 336 are sewn preferably to the outward extremity of the graft 358. When necessary to conserve length of the graft assembly 206, the wire frame pair may be inset inside the tubular graft two to five millimeters from the outward extremity of the graft. The base apices D1 through D8 are spaced equally around the graft. The base helices are slightly compressed when sewn into the graft. When the attachment system is relaxed, the protruding apices extend radially outward past the circumference of the graft in a generally frusto-conical configuration as shown in FIG. 24. This configuration is primarily due to the base apices D1 through D8 being restricted from fully expanding to equilibrium. The protruding apices C1–C6 are not sewn into the graft and expand radially outward farther than the base apices. The circumference of the protruding apices of the attachment system can be adjusted by compressing the protruding apices radially inward. Such adjustment can be accomplished without causing the base apices to respond in an inward direction. This feature improves the fit of the graft in blood vessels that are diseased or similarly do not have smooth lumens with consistent diameters.

Figure 25:
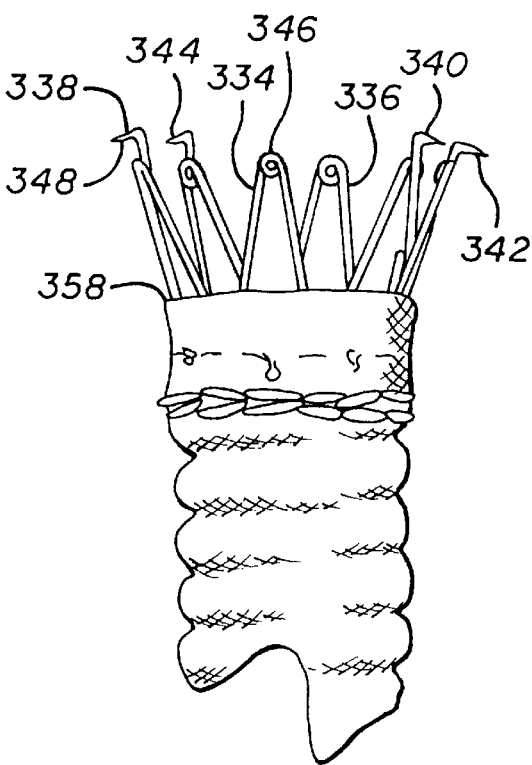
FIG. 25 is a side elevational view of an iliac attachment system, wherein the base apices are sewn within a leg of a bifurcated graft and below the end edge of the leg.
Figure 27:
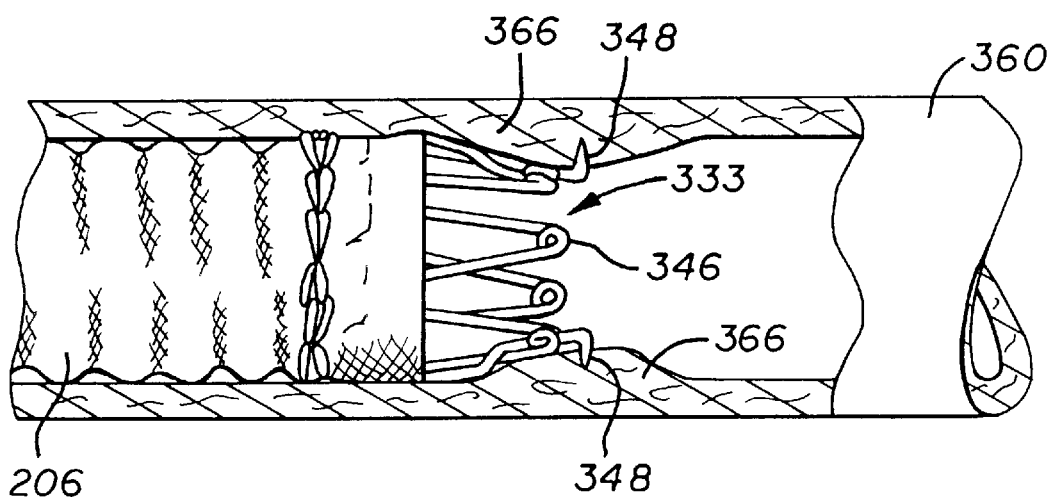
FIG. 27 is a partial cross-sectional view of a leg of a bifurcated graft and an iliac attachment system secured within a vessel having an enlarged vessel wall and constricted lumen.
Figure 28:
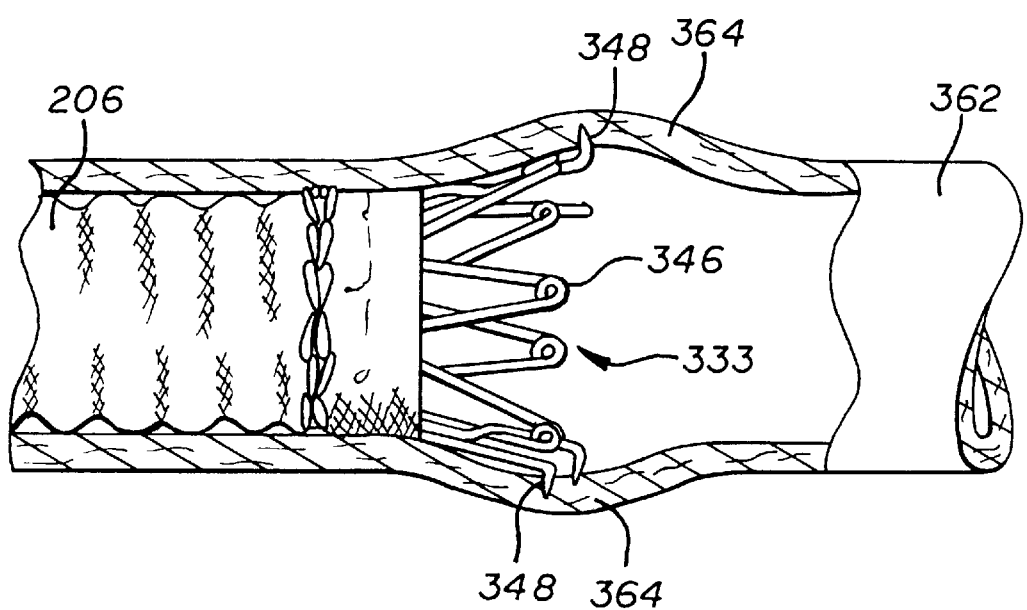
FIG. 28 is a partial cross-sectional view of a leg of a bifurcated graft and an iliac attachment system secured within a vessel having a bulge in the vessel wall.

FIGS. 27 and 28 illustrate the attachment system of FIG. 25 positioned within two diseased blood vessels 360 and 362. The blood vessel in FIG. 28 has a mild bulge 364 providing an increased inside diameter vessel lumen. The normal vessel lumen has an inner diameter comparable in size to the outer diameter of the graft 20 at the end of the graft. The base apices cooperate with the struts to exert an outward bias of the attachment system against the walls of the vessel, securing the end of the graft within the lumen. The diameter of the vessel adjacent to the protruding apices is considerably larger than the diameter of the graft. Since the protruding apices are capable of extending radially outward past the diameter of the graft, the protruding apices are capable of biasing the hooks 348 against the larger diameter lumen.

FIG. 27 shows a vessel where the diameter of the vessel tapers radially inward from the end of the graft to form a constricted area 366. The attachment system 333 remains able to conform to the abnormal shape of the vessel. The protruding apices 346 are capable of being constricted radially inward without eliminating the outward bias exerted by the base helices against the outer periphery of the graft. The ability of the attachment system to adjust to the various shapes of diseased vessels stems from an important design feature that allows each helix to act as point of rotation for the adjacent strut pairs. Consequently, each helix is capable of facilitating the formation of an angle between the adjacent struts with little or no interference caused by the angle of the other struts. This feature in combination with the sinusoidal shape allows the wire frame allows the graft and the attachment system to adapt to a number of abnormally shaped or diseased vessels.

Referring again to FIG. 26, the embodiment illustrated therein includes a cross stitched strand of loosely spun synthetic yarn 368. By loosely spun, it is meant that the individual strands of yarn have a puffy texture with a large amount of surface area exposed. The cross stitched pattern is offset approximately 2 to 5 millimeters longitudinally inward from the end of the graft 206. If the base apices are sewn to the graft inward from the end of the graft as illustrated in FIG. 25, the location of the synthetic yarn will be longitudinally displaced one to five millimeters inward from the row of base apices sewn to the graft. The stitching in this embodiment occurs in a cross hatch or herringbone pattern. The entire circumference of the graft is covered by the synthetic yarn. Because the stitching is located longitudinally inward from the helices, a narrow profile of the compressed graft can be maintained. If, however, the narrow profile of the attachment system can be maintained, the synthetic yarn can be sewn around the perimeter of the graft radially outward from the wire frame.

As viewed in FIG. 29, the graft 206 of the present invention has a plurality of radial crimps 371 spaced longitudinally along at least a portion of the length of the graft. The crimps form a generally corrugated tubular surface defining a plurality of radially outwardly protruding ribs 372 that are separated longitudinally by alternating inwardly directed folds or pleats 374. The distance between each crimp is generally two to three millimeters apart. The radial depth of the ribs is one to two millimeters.

The crimps 371 can be formed by methods known to one skilled in the art such as heat crimping. A crimp iron (not shown) with a heating desired element that is formed into the general shape of the crimping pattern may be placed into the lumen of the graft 206. The graft is tied radially inward at each pleat 374. Finally, the crimp iron is heated causing permanent crimps in the graft. It must be noted that the length of the graft should be adjusted to offset the longitudinal shrinkage caused by heat crimping the graft. For example, a seventy millimeter crimped graft with crimps along twenty millimeters of the graft must use an uncrimped graft that will have a pre-crimped length of about eighty millimeters.

The crimped configuration in the graft 206 has benefits. The crimps 371 prevent kinking in the graft when the graft is deployed in the lumen of angulated vessels. Uncrimped vessels have a greater tendency to form kinks at the angulations, creating an uneven surface within the vessel. Such kinks will cause more turbulence in the vessel.

Another benefit resulting from adding crimps 371 to the graft 206 is due to the patient's respiratory cycle. Certain blood vessels undergo a length change due to the respiratory cycle. The length change of blood vessels may cause considerable stress on the attachment system implanted into the wall of the blood vessel. Crimping of the graft allows a certain longitudinal flexibility of the graft and blood vessel to reduce the stress exerted upon the attachment system.

One of the considerations when determining whether or not to crimp the graft is the goal of spatially distributing the bulk of the graft and the attachment system longitudinally. Because the crimping substantially increases the radial profile of the graft when in a collapsed position, the amount of crimping must be carefully considered. For example, the graft is not crimped along the portion of the graft that surrounds the attachment system. Also, crimps are placed along the graft at locations which are likely to be placed adjacent an angulation of the vessel.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. A system for intraluminally attaching a graft within a vessel, said system comprising:

a generally sinusoidal wire frame configured to be affixed to the graft and to exert an outwardly directed bias, said wire frame having a plurality of alternatively oriented apices, each of said plurality of alternatively oriented apices having a helical configuration; and a plurality of lumen piercing members affixed to said wire frame.

2. A system for intraluminally attaching a graft within a vessel, said system comprising:

a generally sinusoidal wire frame configured to be affixed to the graft and to exert an outwardly directed bias, said wire frame having a plurality of alternatively oriented apices, each of said plurality of alternatively oriented apices having a helical configuration; and a plurality of V-shaped anchoring members cooperating with said wire frame, each of said plurality of V-shaped members having an apex with a helical configuration and ends bent radially outward from said wire frame to form hooks.

3. An intraluminal graft for repairing a vessel having a wall, comprising:

a tubular body;

a generally sinusoidal wire frame affixed to the graft and configured to exert an outwardly directed bias, said wire frame having a plurality of alternatively oriented apices, each of said plurality of alternatively oriented apices having a helical configuration;

a plurality of V-shaped anchoring members cooperating with said wire frame, each of said plurality of V-shaped members having an apex with a helical configuration and ends bent radially outward from said wire frame to form hooks; and a plurality of fibrous tufts affixed to said tubular body, said plurality of fibrous tufts configured to be positioned between the wall of the vessel and the tubular body to limit fluid flow between the wall and the tubular body.

4. An intraluminal graft for repairing a lumen, comprising:

a tubular body;

a generally sinusoidal wire frame affixed to the graft and configured to exert an outwardly directed bias, said wire frame having a plurality of alternatively oriented apices, each of said plurality of alternatively oriented apices having a helical configuration;

a plurality of V-shaped anchoring members cooperating with said wire frame, each of said plurality of V-shaped members having an apex with a helical configuration and ends bent radially outward from said wire frame to form hooks; and a plurality of crimps formed in said tubular body.

5. An attachment system for securing a graft to a blood vessel, the attachment system comprising:

a sinusoidal wire frame having a plurality of apices, said apices being configured with a helical coil spring operating to exert an outwardly directed bias on the wire frame; and a plurality of lumen penetrating members cooperating with said wire frame and responsive to the outwardly directed bias of the same.

6. The attachment system of claim 5, wherein said wire frame has a first terminal end and a second terminal end, said first terminal end being affixed to said second terminal end to provide a continuous wire frame.

7. The attachment system of claim 6, wherein said first terminal end is welded to said second terminal end.

8. The attachment system of claim 6, wherein said first terminal end extends from a first terminal helix and said second terminal end extends from a second terminal helix and said first terminal end is welded to said second terminal end equidistance between said first terminal helix and said second terminal helix.

9. The attachment system of claim 5, wherein said plurality of lumen penetrating members include a generally longitudinally extending arm having a first end and a second end and outwardly protruding hooks extending radially outward from said first end of said arm.

10. The attachment system of claim 9, wherein said outwardly protruding hooks terminate with a sharpened conical tip.

11. The attachment system of claim 9, wherein said outwardly protruding hooks terminate with a duck bill tip.

12. The attachment system of claim 9, wherein said longitudinally extending arms protrude longitudinally beyond at least one of said helical coil springs.

13. The attachment system of claim 5, wherein said wire frame includes a plurality of struts, each of said struts connecting one of said plurality of apices to another of said plurality of apices.

14. The attachment system of claim 13, wherein said lumen penetrating members are individually affixed to one of said struts.

15. The attachment system of claim 14, wherein said lumen penetrating members are individually welded to said struts.

16. The attachment system of claim 15, wherein said lumen penetrating members are welded equidistant between said one of said plurality of apices and said another of said plurality of apices.

17. The attachment system of claim 5, wherein said apices include a first set of apices longitudinally displaced from a second set of apices.

18. The attachment system of claim 17, wherein said first set of apices are all longitudinally aligned.

19. The attachment system of claim 17, wherein said first set of apices are positioned in a longitudinally staggered configuration.

20. The attachment system of claim 17, wherein said second set of apices are all longitudinally aligned.

21. The attachment system of claim 17, wherein said second set of apices are positioned in a longitudinally staggered configuration.

22. The attachment system of claim 5, wherein said lumen penetrating members include first and second generally longitudinally extending arms, said arms protruding longitudinally beyond at least one of said apices and terminating as radially outwardly protruding hooks.

23. The attachment system of claim 22, wherein said apices of said lumen penetrating members is configured with a helical coil.

24. The attachment system of claim 22, wherein said first longitudinally extending arm extends outward at an acute angle from said second longitudinally extending arm.

25. The attachment system of claim 6, wherein said first and second terminal ends are formed with eyelets.

26. The attachment system of claim 25, wherein said first terminal end is configured to overlap said second terminal end.

27. The attachment system of claim 25, wherein said first terminal end extends from a first terminal helix and said second terminal end extends from a second terminal helix, said first terminal end is configured to overlap said second terminal helix and said second terminal end is configured to overlap said first terminal helix.

28. The attachment system of claim 6, wherein said first and second terminal ends are configured with longitudinally extending arms which terminate as radially outward protruding hooks.

29. An attachment system for securing a graft to a blood vessel, the attachment system comprising:
 a first and a second sinusoidal wire frames, each of said wire frames having a pair of terminal ends and further having a plurality of apices, said apices configured with helical coil springs, said first and second wire frames cooperating to exert an outwardly directed bias;
 a plurality of first longitudinally extending arms, each said arm formed at one of said terminal ends of said first wire frame and configured as radially outwardly protruding hooks; and
 a plurality of second longitudinally extending arms, each said arm formed at one of said terminal ends of said second wire frame and configured as radially outwardly protruding hooks.

30. The attachment system of claim 29, further having terminal helices formed at the respective terminal ends of each said first and second wire frames and wherein said first wire frame is joined to said second wire frame such that said terminal helices formed at said terminal ends of said first wire frame overlap the terminal helices formed at said terminal ends of said second wire frame and each of said first plurality of longitudinally extending arms are individually twisted around a portion of said second wire frame and each of said second plurality of longitudinally extending arms are individually twisted around a portion of said first wire frame.

31. An intraluminal graft for repairing a blood vessel comprising:

a graft body having a plurality of ends;
 an attachment system affixed to each said end, each said attachment system further comprising a first and a second sinusoidal wire frame having a plurality of apices, said apices configured with a helical coil spring, each said wire frame cooperating to exert an outwardly directed bias against said graft body, each of said first and second wire frames having a pair of terminal ends; and
 a plurality of first longitudinally extending arms, each said arm formed at one of said terminal ends of said first wire frame and configured as radially outwardly protruding hooks; and
 a plurality of second longitudinally extending arms, each said arm formed at one of said terminal ends of said second wire frame and configured as radially outwardly protruding hooks.

32. The graft of claim 31, wherein each of said first and second longitudinally extending arms protrude longitudinally beyond one of said ends of said graft body.

33. The graft of claim 31, wherein each of said plurality of apices include base apices and longitudinally protruding apices, said base apices are affixed to said graft longitudinally inward from said ends.

34. The graft of claim 31, wherein each of said plurality of apices include base apices and longitudinally protruding apices and said base apices are affixed near one of said ends of said graft body.

35. The graft of claim 31, wherein said graft includes tufts sewn to said graft body near said ends.

36. The graft of claim 35, wherein said tufts are sewn in a cross stitch pattern around an outside surface of said graft body.

37. The graft of claim 36, wherein said tufts are sewn to said graft body longitudinally inward from where said attachment system is affixed to said graft body.

38. A graft for repairing a blood vessel, the graft comprising:
 a graft body having first and second ends;
 a first and a second sinusoidal wire frame, said first frame secured to said first end of said graft body, said second frame secured to said second end of said graft body, said first and second wire frames having a plurality of apices, each of said apices being configured with a helical coil spring operating to exert an outwardly directed bias against the inside wall of said graft body; and
 a plurality of lumen penetrating members, said lumen penetrating members cooperating with at least one of said first and second wire frames and responsive to said outwardly directed bias thereof.

39. The graft of claim 38, wherein each said first and second wire frames have a first end and a second end, said first end being affixed to said second end to provide a continuous wire frame.

40. The graft of claim 39, wherein said first end of each said first and second wire frames overlaps said respective second end.

41. The graft of claim 38, further including tufts secured to an outside surface of said graft body.

42. The graft of claim 41, wherein said tufts are secured to said graft body longitudinally inward from where said first and second wire frames are affixed to said graft body.

43. The graft of claim 41, wherein said tufts are sewn in a cross stitch pattern.

44. The graft of claim 41, wherein said tufts are made of dacron wool.

45. The graft of claim 41, wherein said first and second wire frames include struts connecting one of said helices to another of said helices and said tufts are secured to said body generally between said struts.

46. The graft of claim 38, wherein said graft includes laterally extending pleats.

47. The graft of claim 46, wherein said pleats are located longitudinally inward from where said first and second wire frames are secured to said graft body.

48. The graft of claim 38, wherein said first and second wire frames are configured to be sewn to an inside wall of said graft body.

49. The graft of claim 48, wherein a portion of said first wire frame protrudes longitudinally past said first end of said graft body, and a portion of said second wire frame protrudes longitudinally past said second end of said graft body.

50. The graft of claim 38, wherein said lumen penetrating members include first and second generally longitudinally extending arms projecting from a helical coil formed at an apex of said lumen penetrating members and terminating in radially outwardly protruding hooks.

51. The graft of claim 50, wherein said lumen penetrating members are sewn to an inside wall of said graft body.

52. The graft of claim 50, wherein said lumen penetrating members are mounted to said graft body by passing said first and second arms through a wall of said graft body to thereby position said apex of said lumen penetrating member on an outside of said graft body and at least a portion of said first and second arms inside said graft body.

53. The graft of claim 52, wherein tufts are affixed to said apices of said lumen penetrating member.

54. The graft of claim 50, wherein said plurality of apices of said first and second wire frames include base apices and said lumen penetrating members are mounted to said graft body such that said apices of said lumen penetrating members is positioned longitudinally along said graft body between at least one of said ends of said graft body and where at least one of said base apices is positioned along said graft body, said helical coils of said wire frames having a diameter greater than said helical coils of said lumen penetrating members.

55. The graft of claim 38, wherein each of said wire frames have a first terminal end and a second terminal end, said first and second terminal ends being formed with first and second terminal eyelets, respectively.

56. The graft of claim 55, wherein said first terminal end is configured to overlap said second terminal end.

57. The graft of claim 55, wherein said first terminal ends are configured to overlap one of said second terminal eyelets and said second terminal ends are configured to overlap one of said first terminal eyelets.

58. The graft of claim 38 wherein said graft body includes a plurality of laterally extending pleats.

59. The graft of claim 58, wherein said pleats cover less than half of the length of said graft body.

60. An intraluminal graft for repairing a blood vessel, the graft comprising:
   a graft body having an inner surface and an outer surface;
   a sinusoidal wire frame having a plurality of apices and a plurality of struts, each of said struts connecting one of said apices to another of said apices, said apices and struts operating to exert an outwardly directed bias against the inner surface of said graft body; and
   a plurality of tufts that are discrete from the fabric of the graft body and are selectively affixed to said outer surface of said graft body.

61. The graft of claim 60, wherein each of said tufts are positioned longitudinally along said outer surface of said graft body inward from where said wire frame is positioned longitudinally along said body.

62. The graft of claim 60, wherein said tufts are affixed to said outside surface of said graft body generally between said struts.

63. The attachment system of claim 5, wherein the lumen penetrating members are V-shaped having first and second arms.

64. The attachment system of claim 5, wherein the lumen penetrating members have a radially outward protruding hook at the end of each said arm.

65. The attachment system of claim 29, wherein said hooks terminate with a sharpened conical tip.

66. The attachment system of claim 29, wherein said hooks terminate with a duck bill tip.

67. The attachment system of claim 29, wherein said longitudinally extending arms protrude longitudinally beyond at least one of said helical coil springs.

68. The attachment system of claim 29, wherein said first sinusoidal wire frame has first terminal apices adjacent said first longitudinally extending arms and said second sinusoidal wire frame has second terminal apices adjacent said second sinusoidal wire frame, said first terminal apices are configured to overlap said second terminal apices.

69. The attachment system of claim 31, wherein said hooks terminate with a sharpened conical tip.

70. The attachment system of claim 31, wherein said hooks terminate with a duck bill tip.

71. The attachment system of claim 31, wherein said longitudinally extending arms protrude longitudinally beyond at least one of said helical coil springs.

72. The attachment system of claim 31, wherein said first sinusoidal wire frame has a first terminal apices adjacent said first longitudinally extending arms and said second sinusoidal wire frame has second terminal apices adjacent said second longitudinally extending arm, said first terminal apices are configured to overlap said second terminal apices.

73. An attachment system for securing a graft to a blood vessel, the attachment system comprising:
   a first and a second sinusoidal wire frames, said wire frames having a pair of terminal ends and further having a plurality of apices, said first and second wire frames cooperate to exert an outwardly directed bias;
   a plurality of first longitudinally extending arms formed at one of said terminal ends of said first wire frame and configured as radially outwardly protruding hooks; and
   a plurality of second longitudinally extending arms, each said arm formed at one of said terminal ends of said second wire frame and configured as radially outwardly protruding hooks.

74. The attachment system of claim 73, further having terminal apices formed adjacent the respective terminal ends of each said first and second wire frames and wherein said first wire frame is joined to said second wire frame such that said terminal apices formed adjacent said terminal ends of said first wire frame overlap the terminal apices formed adjacent said terminal ends of said second wire frame and each of said first plurality of longitudinally extending arms are individually twisted around a portion of said second wire frame and each of said second plurality of longitudinally extending arms are individually twisted around a portion of said first wire frame.

75. The attachment system of claim 73, wherein said hooks terminate with a sharpened conical tip.

76. The attachment system of claim 73, wherein said hooks terminate with a duck bill tip.

77. The attachment system of claim 73, wherein said plurality of apices are defined by helical coil springs and said longitudinally extending arms protrude longitudinally beyond at least one of said helical coil springs.

78. The attachment system of claim 73, wherein said first sinusoidal wire frame has a first terminal apices adjacent said first longitudinally extending arms and said second sinusoidal wire frame has second terminal apices adjacent said second longitudinally extending arms, said first terminal apices are configured to overlap said second terminal apices.

79. An intraluminal graft for repairing a blood vessel comprising:
a graft body having a plurality of ends;
an attachment system affixed to each end, said attachment system further comprising a first and a second sinusoidal wire frame having a plurality of apices, each said wire frame cooperating to exert an outwardly directed bias against said graft body, each of said first and second wire frames having a pair of terminal ends; and
a plurality of first longitudinally extending arms, each said arm formed at one of said terminal ends of said first wire frame and configured as radially outwardly protruding hooks; and
a plurality of second longitudinally extending arms, each said arm formed at one of said terminal ends of said second wire frame and configured as radially outwardly protruding hooks.

80. The graft of claim 79, wherein each of said first and second longitudinally extending arms protrude longitudinally beyond one of said ends of said graft body.

81. The graft of claim 79, wherein each of said plurality of apices include base apices and longitudinally protruding apices, said base apices are affixed to said graft longitudinally inward from said ends.

82. The graft of claim 79, wherein each of said plurality of apices include base apices and longitudinally protruding apices and said base apices are affixed near one of said ends of said graft body.

83. The graft of claim 79, wherein said graft includes tufts sewn to said graft body near said ends.

84. The graft of claim 83, wherein said tufts are sewn in a cross stitch pattern around an outside surface of said graft body.

85. The graft of claim 84, wherein said tufts are sewn to said graft body longitudinally inward from where said attachment system is affixed to said graft body.

86. The attachment system of claim 79, wherein each of said hooks terminate with a sharpened conical tip.

87. The attachment system of claim 79, wherein each of said hooks terminate with a duck bill tip.

88. The attachment system of claim 79, wherein said plurality of apices are defined by helical coil springs and each of said longitudinally extending arms protrude longitudinally beyond at least one of said helical coil springs.

89. The attachment system of claim 79, wherein said first sinusoidal wire frame has a first terminal apices adjacent said first longitudinally extending arms and said second sinusoidal wire frame has second terminal apices adjacent said first longitudinally extending arms and said first terminal apices are configured to overlap said second terminal apices.

90. An attachment system for securing a graft to a blood vessel, the attachment system comprising:
a sinusoidal wire frame having a plurality of apices operating to exert an outwardly directed bias on the wire frame; and
a plurality of V-shaped lumen penetrating members cooperating with said wire frame and responsive to the outwardly directed bias of the same.

91. The attachment system of claim 90, wherein said wire frame has a first terminal end and a second terminal end, said first terminal end being affixed to said second terminal end to provide a continuous wire frame.

92. The attachment system of claim 91, wherein said first terminal end is welded to said second terminal end.

93. The attachment system of claim 91, wherein said first terminal end extends from a first terminal apex and said second terminal end extends from a second terminal apex and said first terminal end is welded to said second terminal end equidistance between said first terminal apex and said second terminal apex.

94. The attachment system of claim 90, wherein said plurality of V-shaped lumen penetrating members include radially outwardly protruding hooks extending therefrom.

95. The attachment system of claim 94, wherein said outwardly protruding hooks terminate with a sharpened conical tip.

96. The attachment system of claim 94, wherein said outwardly protruding hooks terminate with a duck bill tip.

97. The attachment system of claim 96, wherein said longitudinally extending arms protrude longitudinally beyond at least one of said helical coil springs.

98. The attachment system of claim 90, wherein said apices include a first set of apices longitudinally displaced from a second set of apices.

99. The attachment system of claim 98, wherein said first set of apices are all longitudinally aligned.

100. The attachment system of claim 98, wherein said first set of apices are positioned in a longitudinally staggered configuration.

101. The attachment system of claim 98, wherein said second set of apices are all longitudinally aligned.

102. The attachment system of claim 98, wherein said second set of apices are positioned in a longitudinally staggered configuration.

103. The attachment system of claim 91, wherein said first and second terminal ends are formed with eyelets.

104. The attachment system of claim 103, wherein said first terminal end is configured to overlap said second terminal end.

105. The attachment system of claim 103, wherein said first terminal end extends from a first terminal apex and said second terminal end extends from a second terminal apex, said first terminal end is configured to overlap said second terminal apex and said second terminal end is configured to overlap said first terminal apex.

* * * * *

UNITED STATES PATENT AND TRADEMARK OFFICE
CERTIFICATE OF CORRECTION

PATENT NO. : 6,221,102 B1
DATED : April 24, 2001
INVENTOR(S) : Steven G. Baker, et al.

It is certified that error appears in the above-identified patent and that said Letters Patent is hereby corrected as shown below:

Column 19,
Line 64, change "FIG. 1A", to read -- FIG. 19 --.

Column 24,
Line 45, after "frame", add -- and ending with apex closest to the second end 344 --.
Lines 45 & 46, delete "and ending with apex closest to the second end 344".

Column 26,
Line 24, before "the wire", delete "allows", add -- of --

Column 28, claim 14,
Lines 59 & 60, delete "one of".

Signed and Sealed this

Thirtieth Day of October, 2001

Attest:

NICHOLAS P. GODICI
*Attesting Officer*    *Acting Director of the United States Patent and Trademark Office*